US009109015B2

(12) United States Patent
Romero et al.

(10) Patent No.: US 9,109,015 B2
(45) Date of Patent: Aug. 18, 2015

(54) METHOD OF ISOLATING BIOMACROMOLECULES USING LOW PH AND DIVALENT CATIONS

(75) Inventors: Jonathan Romero, Somerville, MA (US); James Chrostowski, Winchester, MA (US); Philippe Georges De Vilmorin, Arlington, MA (US); Jennifer Yun Case, Milton, MA (US)

(73) Assignee: BIOGEN MA INC, Cambridge, MA (US)

( * ) Notice: Subject to any disclaimer, the term of this patent is extended or adjusted under 35 U.S.C. 154(b) by 1381 days.

(21) Appl. No.: 12/513,137

(22) PCT Filed: Nov. 1, 2007

(86) PCT No.: PCT/US2007/023028
§ 371 (c)(1),
(2), (4) Date: Feb. 1, 2010

(87) PCT Pub. No.: WO2008/127305
PCT Pub. Date: Oct. 23, 2008

(65) Prior Publication Data
US 2010/0145022 A1 Jun. 10, 2010

Related U.S. Application Data

(60) Provisional application No. 60/855,734, filed on Nov. 1, 2006, provisional application No. 60/935,545, filed on Aug. 17, 2007.

(51) Int. Cl.
C07K 17/00 (2006.01)
C07K 16/06 (2006.01)
C07K 1/34 (2006.01)

(52) U.S. Cl.
CPC .............. *C07K 16/065* (2013.01); *C07K 1/34* (2013.01)

(58) Field of Classification Search
None
See application file for complete search history.

(56) References Cited

U.S. PATENT DOCUMENTS

| 4,164,495 A | 8/1979 | Hansen |
| 4,177,188 A | 12/1979 | Hansen |
| RE31,268 E | 6/1983 | Hansen |
| 4,801,687 A | 1/1989 | Ngo |
| 4,814,091 A | 3/1989 | Napier et al. |
| 4,841,024 A | 6/1989 | Nathans et al. |
| 4,849,352 A | 7/1989 | Sullivan et al. |
| 4,933,435 A | 6/1990 | Ngo |
| 4,939,176 A | 7/1990 | Seng et al. |
| 5,110,913 A | 5/1992 | Coan et al. |
| 5,151,504 A | 9/1992 | Croze |
| 5,164,487 A | 11/1992 | Kothe et al. |
| 5,429,746 A | 7/1995 | Shadle et al. |
| 5,468,847 A | 11/1995 | Heilmann et al. |
| 5,760,189 A * | 6/1998 | Vicik et al. ............... 530/412 |
| 6,846,410 B2 | 1/2005 | McNeff et al. |
| 6,870,034 B2 | 3/2005 | Breece et al. |
| 6,995,246 B1 | 2/2006 | Wan et al. |
| 7,038,017 B2 | 5/2006 | Rinderknecht et al. |
| 7,064,191 B2 | 6/2006 | Shinkawa et al. |
| 2005/0272917 A1 | 12/2005 | Jiao et al. |
| 2008/0248047 A1 | 10/2008 | Das et al. |
| 2008/0254043 A1 | 10/2008 | Umemura et al. |

FOREIGN PATENT DOCUMENTS

| CN | 1146730 A | 4/1997 |
| CN | 1752036 A | 3/2006 |
| JP | 2006-513144 A | 4/2006 |
| WO | WO 91/10678 | 7/1991 |
| WO | WO 95/22389 | 8/1995 |
| WO | WO 2004/022581 A1 | 3/2004 |
| WO | WO 2006/082974 A1 | 8/2006 |

OTHER PUBLICATIONS

De Frutos, M., et al., "Aggregation of Nucleosomes by Divalent Cations," *Biophys. J.* 81:1127-1132, the Biophysical Society, United States (2001).
Hardy R.R., "Purification and Characterization of Monoclonal Antibodies," *Immunochemistry* 1:13.1-13.13, Pergamon Press, United States (1986).
Lydersen, B.K., et al., "Acid Precipitation of Mammalian Cell Fermentation Broth," *Ann. N.Y. Acad. Sci.* 745:222-231, New York Academy of Sciences, United States (1994).
McKinney, M.M. and Parkinson, A., "A simple, non-chromatographic procedure to purify immunoglobulins from serum and ascites fluid," *J. Immunol. Methods* 96:271-278, Elsevier Science Publishers B.V., Netherlands (1987).
Nifong, T.P. and Gerhard, G.S., "Separation of IgG and IgM from Albumin in Citrated Human Plasma Using Electrodialysis and Metal Ion Affinity Precipitation," *ASAIO J.* 48:645-649, Lippincott Williams & Wilkins, United States (2002).
Weisenberg, R.C. and Timasheff, S.N., "Aggregation of Microtubule subunit protein. Effects of Divalent Cations, Colchicine and Vinblastine," *Biochemistry* 9:4110-4116, American Chemical Society, United States (1970).
International Search Report for International Application No. PCT/US07/23028, International Searching Authority, Alexandria, Virginia, USA, mailed on Dec. 31, 2008, 3 pages.
Written Opinion of the International Searching Authority for International Application No. PCT/US2007/023028, International Searching Authority, Alexandria, Virginia, USA, mailed on Dec. 31, 2008, 4 pages.
Lian, Xi-Jun, et al., "The Effect of pH and Metal Ions on Gelatin Formation of Soybean Protein Isolate," *Cereals & Oils* (10):75-78, Tsinghua Tongfang Knowledge Network Technology Co., Ltd., China (2006) (Abstract only in English).
English language Abstract of Chinese Patent Publication No. CN 1752036 A, European Patent Office, espacenet database—Worldwide (2006).
Unknown Author, "Tanpakushitu I [Protein I]—Separation, Purification, Characteristic," pp. 128 (1990).
English language translation for "Tanpakushitu [Protein I]—Separation, Purification, Characteristic," pp. 128 (1990) (listed as document NPL11).

\* cited by examiner

*Primary Examiner* — Yunsoo Kim
(74) *Attorney, Agent, or Firm* — Sterne, Kessler, Goldstein and Fox PLLC

(57) ABSTRACT

The present invention is related to a method of isolating a biological macromolecule in a composition. Specifically, the present invention is directed to a method of isolating a biomacromolecule in a composition containing an impurity, the method comprising (a) lowering the pH of the composition, (b) adding a divalent cation to the composition, and (c) separating the biomacromolecule from the impurity.

24 Claims, 18 Drawing Sheets

FIG. 5a
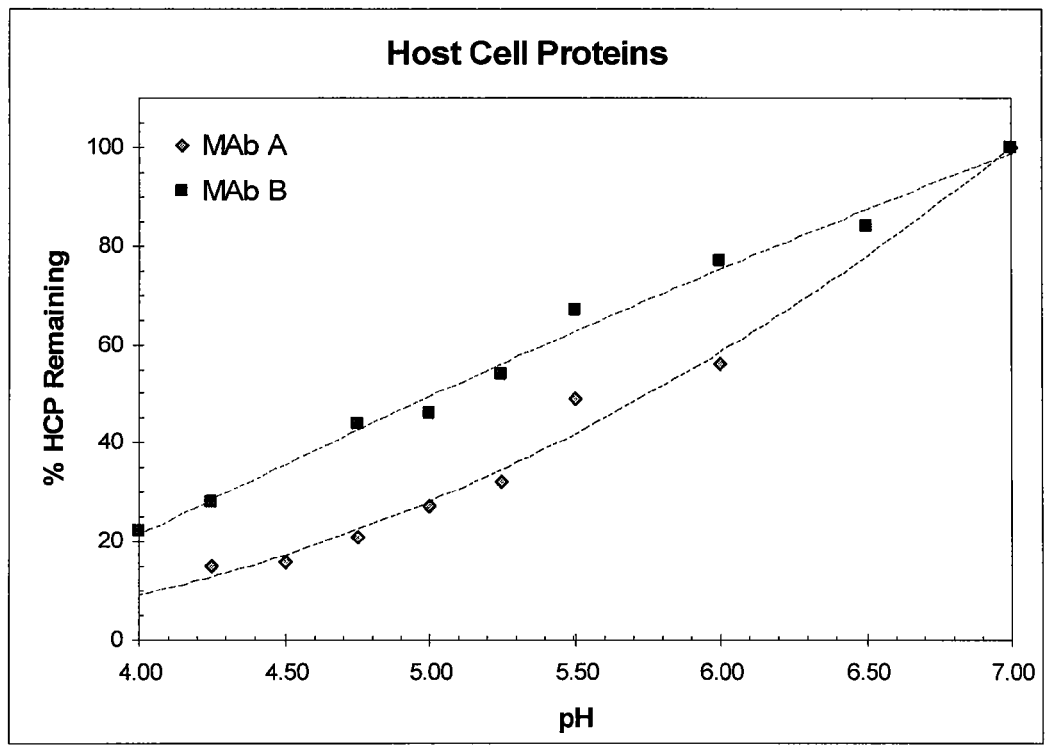
FIG. 5b
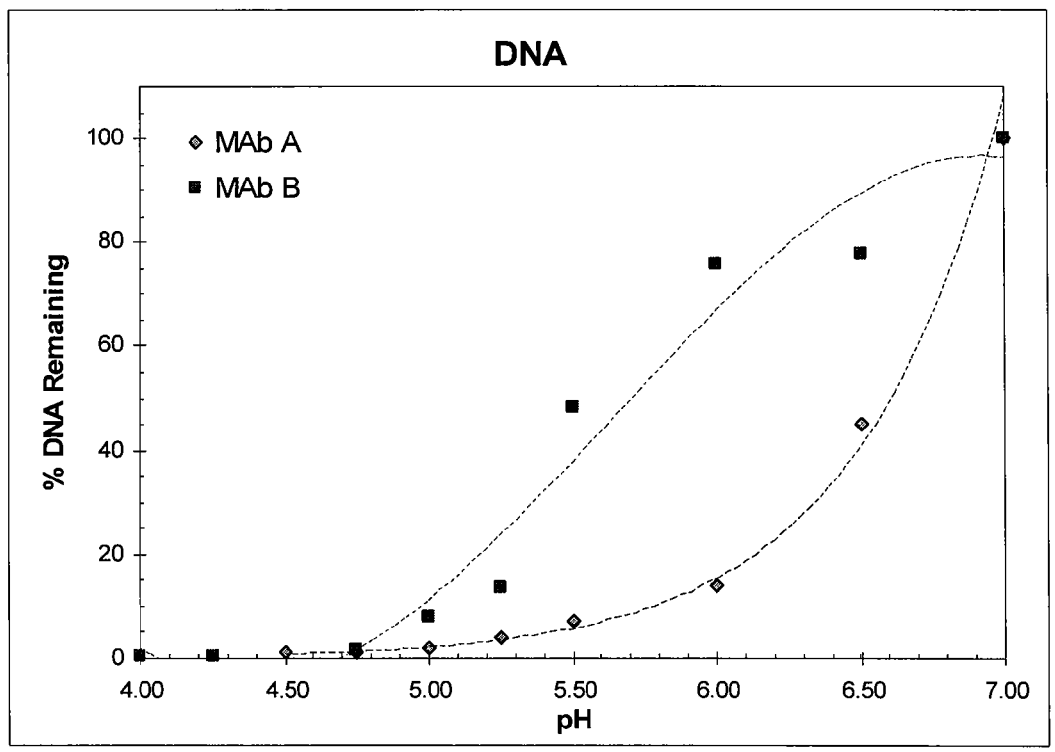
FIG. 5

FIG. 6a
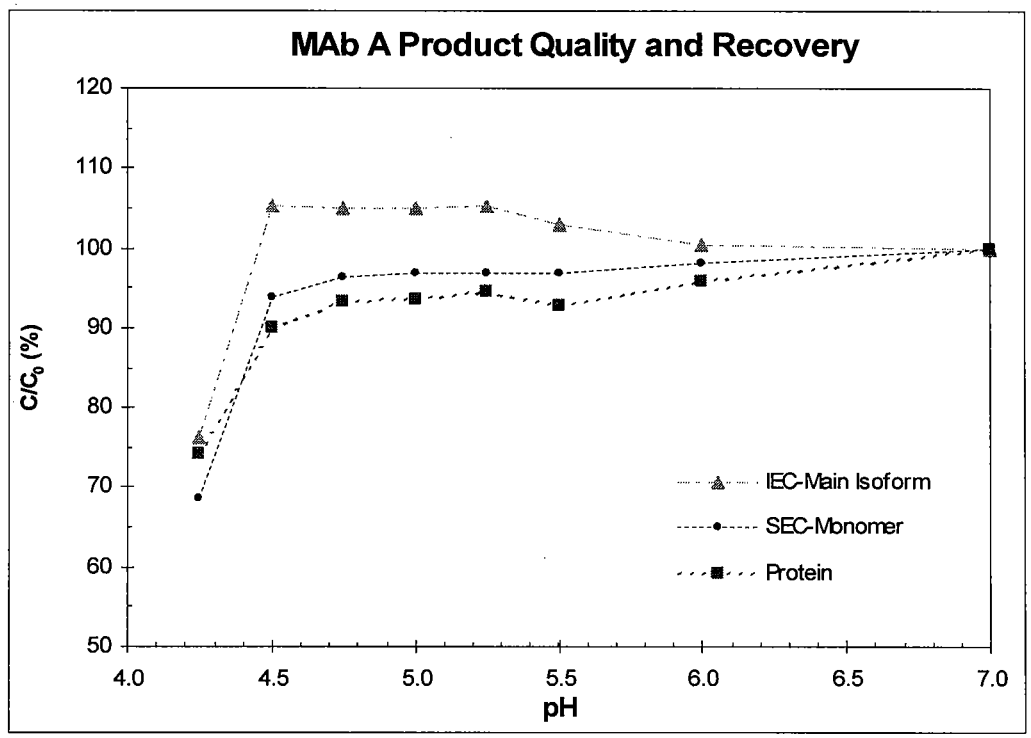
FIG. 6b
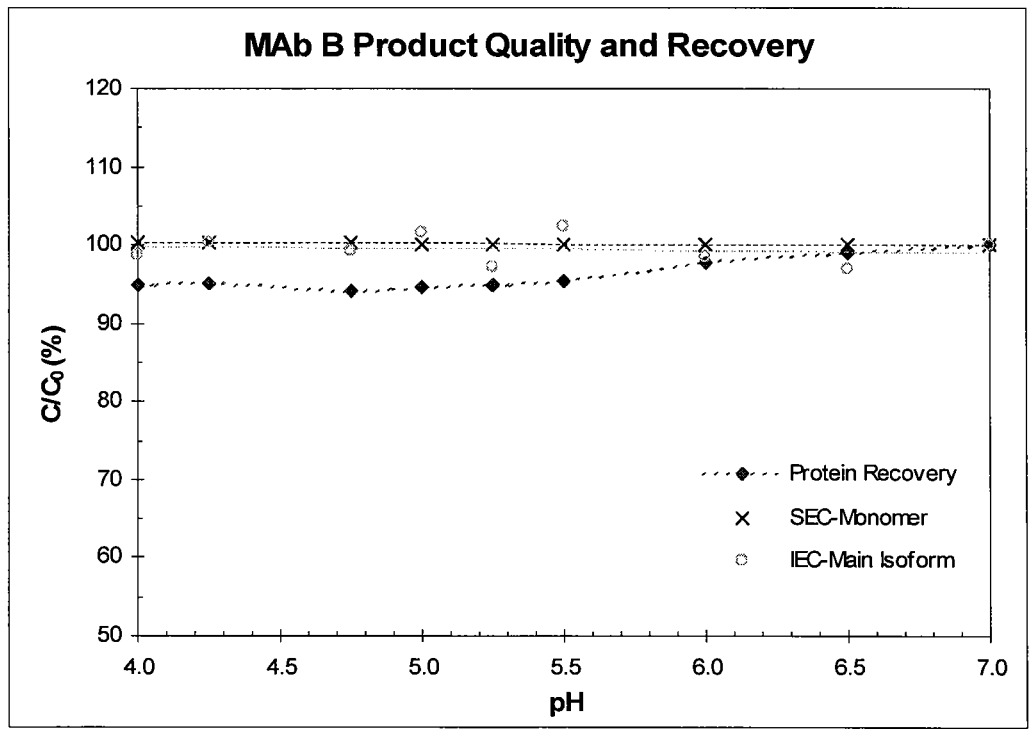
FIG. 6

- Constant Retentate or Recirculation Flowrate establish with Pump
- Constant Permeate Flowrate establish with Pump

METHOD OF ISOLATING BIOMACROMOLECULES USING LOW PH AND DIVALENT CATIONS

This application is the National Stage of International Application No. PCT/US2007/023028, filed Nov. 1, 2007, which published as WO 2008/127305 in English on Oct. 23, 2008, and which claims the benefit of U.S. Provisional Application 60/855,734, filed Nov. 1, 2006; and U.S. Provisional Application No. 60/935,545, filed Aug. 17, 2007, all of the above applications are incorporated herein by reference in their entireties.

BACKGROUND OF THE INVENTION

1. Field of the Invention

The present invention is related to a method of isolating a biological macromolecule in a composition. Specifically, the present invention is directed to a method of isolating a biomacromolecule in a composition containing an impurity, the method comprising (a) lowering the pH of the composition, (b) adding a divalent cation to the composition, and (c) separating the biomacromolecule from the impurity.

2. Background Art

Biological macromolecules (i.e., biomacromolecules) such as recombinant biomacromolecules have importance in a diverse array of technologies. Traditionally, biomacromolecules have been purified using many different methods, e.g., filtration, centrifugation, size exclusion chromatography, affinity chromatography, and combinations of the above, just to name a few. The method of purification is generally chosen based on a characteristic of the biomacromolecule that distinguishes it from one or more impurities that coexist with the biomacromolecule in a composition. A vast number of biomacromolecules are commercially important, and an ability to purify a large amount of biomacromolecules in a timely and cost effective manner is desired. Extensive research has been performed to increase efficiency of current purification technologies and methods for purifying biomacromolecules. Often, purification techniques that are suitable for small scale preparations are not suitable for industrial-scale purification.

Commercially important biomacromolecules include, e.g., proteins and nucleic acids, e.g., DNA and RNA. Two examples of biomacromolecules that are often isolated on an industrial scale are monoclonal antibodies and fusion proteins. These antibodies and fusion proteins are valuable in various diagnostic and therapeutic fields, and have been used to treat various diseases such as inherited and acquired immune-deficiency diseases and infectious diseases.

Traditional approaches to producing purified antibodies include ammonium sulfate precipitation, use of caprylic acid followed by centrifugation, ion exchange chromatography (e.g., DEAE or hydroxyapatite), immunoaffinity purification (e.g., protein A or protein G), and dialysis. See e.g., *Antibodies: A Laboratory Manual*, Harlow and Lane, Cold Spring Harbor Laboratory (1988). The use of a combination of the above methods is common, e.g., antibody purification from plasma using ethanol fractionation followed by ion exchange chromatography and/or caprylic acid (CA) precipitation. See for example McKinney et al., *J. Immunol. Methods* 96:271-278 (1987); U.S. Pat. Nos. 4,164,495; 4,177,188; RE 31,268; 4,939,176; and 5,164,487. In addition, acidification of fermentation has been used to improve recovery and stability of antibodies and recombinant proteins. See e.g., Lydersen et al., *Annals New York Academy of Sciences* 745:222-31 (1994).

Various other methods have been developed for isolation and/or purification of antibodies including the application of acid precipitation. See e.g., U.S. Pat. Nos. 7,038,017; 7,064,191; 6,846,410; 5,429,746; 5,151,504; 5,110,913; 4,933,435; 4,841,024; and 4,801,687. However, many of these methods can result in large feedstock volumes and recovery loss and/or have a high cost for producing antibodies on industrial scales. Limited work has exploited the benefits of adjusting harvest conditions to improve cellular clarification robustness, especially as it pertains to tangential flow filtration.

The harvesting of antibodies and recombinant proteins from industrial-scale bioreactors containing mammalian or bacterial cells is generally performed using either filtration or centrifugation. However, in the case of these techniques, nucleic acid (e.g., DNA), host cell proteins (HCP), and growth media components are often not adequately separated from the biomacromolecule of interest. The recent drive for generating increased amounts of protein production in cell culture has required bioreactors to operate at higher cell densities, which increases the amount of impurities such as DNA, HCP, and other media components. The elevated levels of contaminants have placed stronger demands on both cell harvesting operations (e.g., the filtration and centrifugations steps), as well as the downstream purification steps (e.g., chromatography and dialysis steps). The addition of these higher levels of impurities may increase the number of purification steps that need to be performed, thus decreasing overall production throughput.

As a result of the aforementioned difficulties and inefficiencies, there is a need to improve the strategy for isolation of biomacromolecules.

BRIEF SUMMARY OF THE INVENTION

The present invention is directed to a method of isolating a biomacromolecule in a composition containing an impurity, the method comprising: (a) lowering the pH of the composition; (b) adding a divalent cation to the composition; and (c) separating the biomacromolecule from the impurity. In some embodiments, the lowering the pH of (a) and the adding a divalent cation of (b) occurs before the separating of (c).

The separating of the biomacromolecule can be achieved by various means. In some embodiments, the separating of (c) is performed by filtering the composition, the filtering forming a permeate stream and a retentate stream. In some embodiments where filtration is used, the biomacromolecule is substantially in the permeate stream and in some embodiments, the filtering is performed by a tangential-flow filter. In other embodiments, the separating of (c) is performed by subjecting the composition to centrifugation, the centrifugation forming a supernatant and a precipitate. In some embodiments where centrifugation is used, the biomacromolecule is substantially in the supernatant.

In some aspects of the present invention, the pH of the composition in (a) is lowered at least 1 pH unit. In some aspects of the present invention, the pH of the composition in (a) is adjusted to a pH within a range of about 3.0 to about 6.5, about 3.0 to about 5.0, or about 4.0 to about 4.7.

In some aspects of the present invention, the biomacromolecule is a protein. In some embodiments, the protein is a soluble protein. In some embodiments, the protein is an antibody. In some embodiments, the composition comprises eukaryotic cellular material. In some embodiments, the impurity comprises a protein, lipid, nucleic acid, ribonucleic acid, or combinations thereof.

Various divalent cations can be used in the present invention. In some embodiments, the divalent cation is selected from the group consisting of $Ca^{2+}$, $Mg^{2+}$, $Cu^{2+}$, $Co^{2+}$, $Mn^{2+}$, $Ni^{2+}$, $Be^{2+}$, $Sr^{2+}$, $Ba^{2+}$, $Ra^{2+}$, $Zn^{2+}$, $Cd^{2+}$, $Ag^{2+}$, $Pd^{2+}$, $Rh^{2+}$ and combinations thereof. In some embodiments, the divalent cation is selected from the group consisting of $Ca^{2+}$, $Mg^{2+}$, $Cu^{2+}$, $Co^{2+}$, $Mn^{2+}$ or combinations thereof. In some embodiments, the composition comprises a divalent cation concentration of about 1 mM to about 100 mM, or about 2 mM to about 50 mM.

Some aspects of the present invention are directed to a method of isolating a biomacromolecule wherein the addition of the divalent cation increases the recovery of the biomacromolecule by greater than 3%. In some embodiments, the recovery of the biomacromolecule is increased greater than 10%.

In some embodiments of the present invention the separating is performed by filtering the composition, wherein the filtering results in a transmembrane pressure; and wherein the transmembrane pressure remains substantially constant during the filtering.

In some embodiments of the present invention, the pH of said composition is lowered to a pH of 3.0 to 5.0; the divalent cation is selected from the group consisting of $Ca^{2+}$, $Mg^{2+}$, $Cu^{2+}$, $Co^{2+}$, $Mn^{2+}$ or combinations thereof; the separating is performed by filtering said composition; and the biomacromolecule is an antibody.

In some embodiments, the invention is directed to a method of purifying a biomacromolecule in a composition containing an impurity, the method comprising: (a) lowering the pH of said composition; (b) adding a divalent cation to said composition; and (c) separating said biomacromolecule from said impurity in said composition. In some embodiments, the invention is directed to a method of clarifying a composition containing a biomacromolecule and an impurity, the method comprising: (a) lowering the pH of said composition; (b) adding a divalent cation to said composition; and (c) separating said biomacromolecule from said impurity in said composition.

BRIEF DESCRIPTION OF THE DRAWINGS/FIGURES

Figure 4:
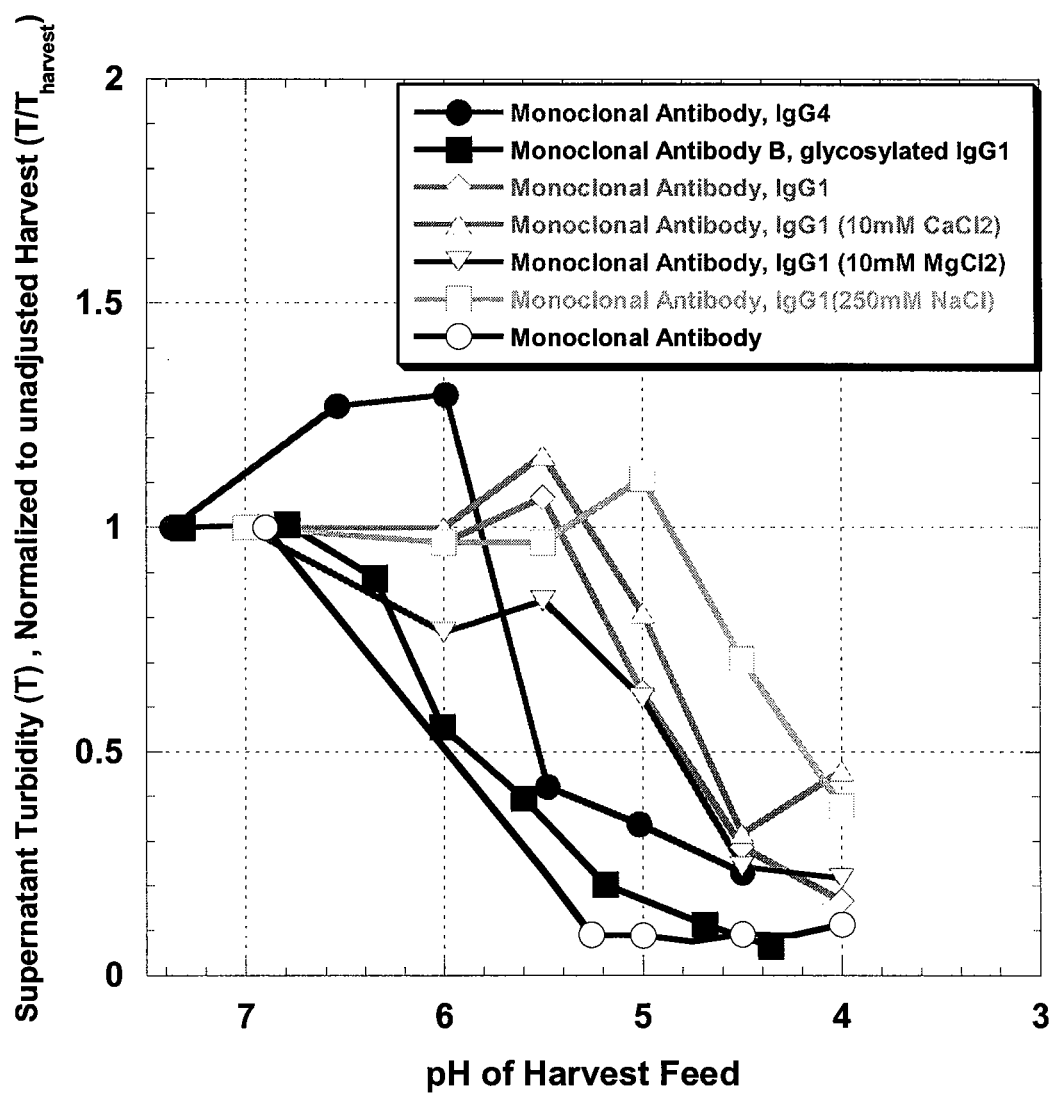

FIG. 4 represents the effect of pH adjustment of the harvest feed on turbidity of the supernatant. The y-axis represents the turbidity of the supernatant after harvest pH adjustment and settling of flocculated cells+cell debris. The x-axis represents the various pH adjustment values of the harvest material. In particular, the data was generated by pH adjusting aliquots of harvest feed to the specified pH using 25% v/v acetic or citric acid, allowing flocculation and settling of the cellular mass to occur, and measuring the turbidity (degree of clarity) of the clear supernatant. The data in FIG. 4 is generated from various harvest streams containing different recombinant proteins including antibodies and fusion proteins. The graph demonstrates a general reduction on supernatant turbidity as the pH of the adjusted harvest material drops, indicating a clearer supernatant at lower pH value. This is a result of higher degree of cellular flocculation that occurs at lower pH resulting in more rapid settling of the cellular mass. This flocculation and improved settling provides for improved mass transfer near membrane surface and thus more efficient microfiltration operational performance (See FIG. 12 and FIG. 13).

FIG. 5 represents the effect of various pH levels on removal of host cell proteins (FIG. 5a) and DNA (FIG. 5b) from two separate cell culture, the cell cultures producing antibodies A and B. The x-axis represents the various pH adjustment values of the cell culture. The y-axis represents the % of either host cell protein or DNA remaining in the sample.

FIG. 6 represents the effect of various pH levels on product quality and recovery for two different monoclonal antibodies, A (FIG. 6a) and B (FIG. 6b). The x-axis represents the various pH adjustment values of the cell culture. For the MabA graph (FIG. 6a), the squares represent protein recovery, the circles represent SEC monomers, and the triangles represent IRC main isoforms. For the Mab B graph (FIG. 6b), the diamonds represent protein recovery, the Xs represent SEC monomers, and the circles represent IEC main isoforms.

Figure 7:
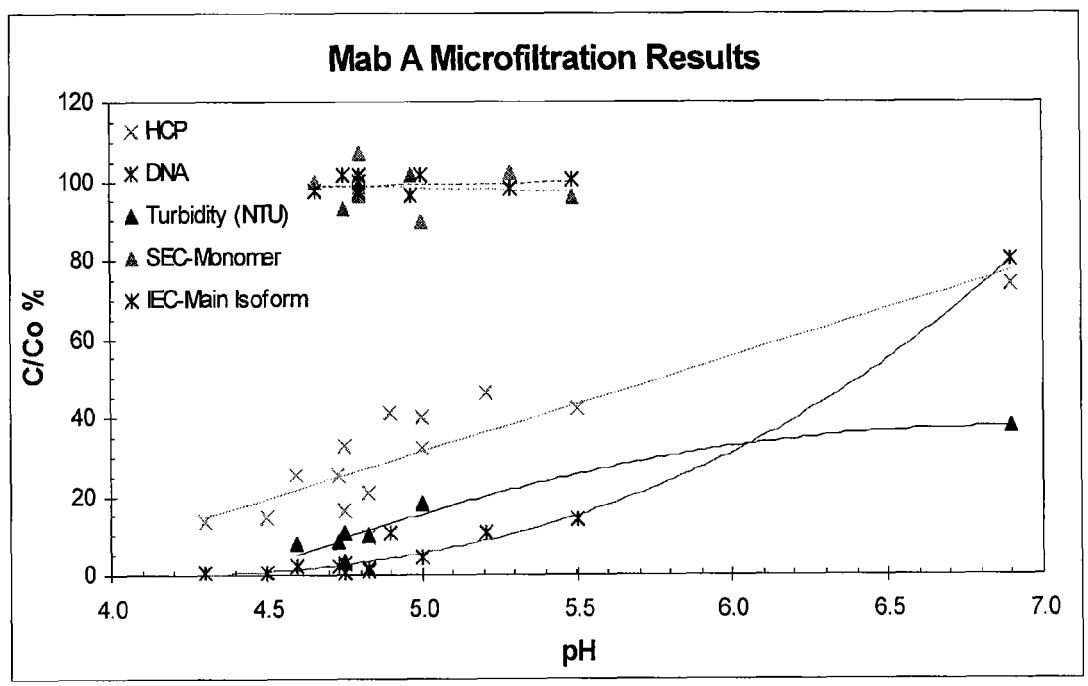

FIG. 7 represents the effect of various pH levels on microfiltration performance. The x-axis represents the various pH adjustment values of the cell culture. The Xs represent concentration percentages of host cell proteins, the stars represent concentrations of DNA, the dark triangles represent turbidity, the light triangles represent SEC monomers, and the astericks represent IEC main isoforms.

Figure 8:
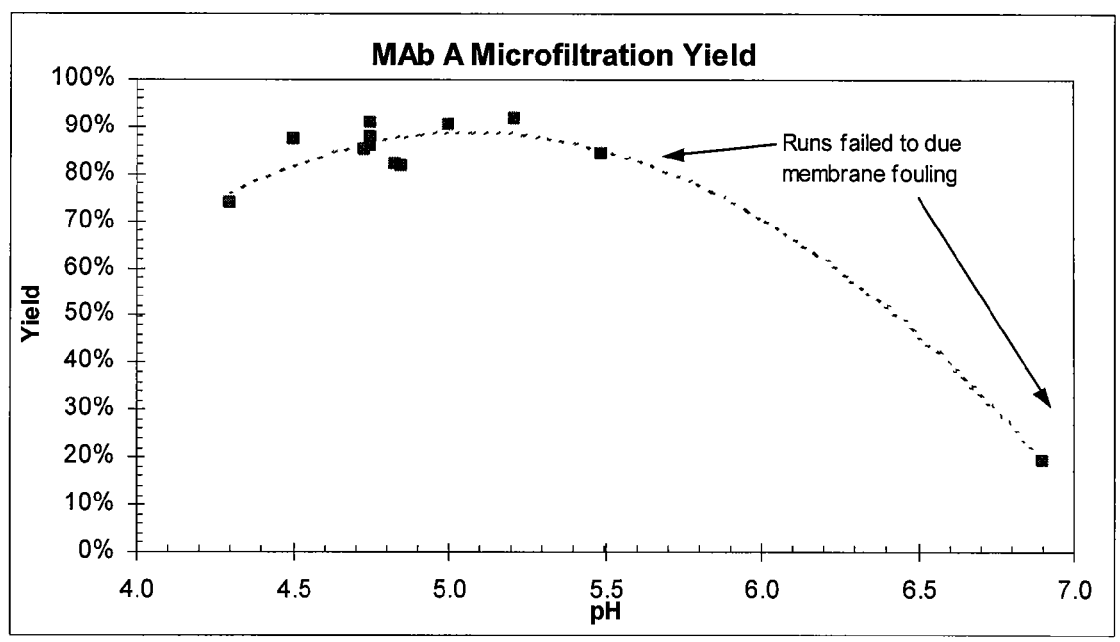

FIG. 8 represents the effects of various pH levels on the yield of monoclonal antibody A after microfiltration. The measurements at pH levels greater than 5.5 failed due to fouling of the membrane.

Figure 9:
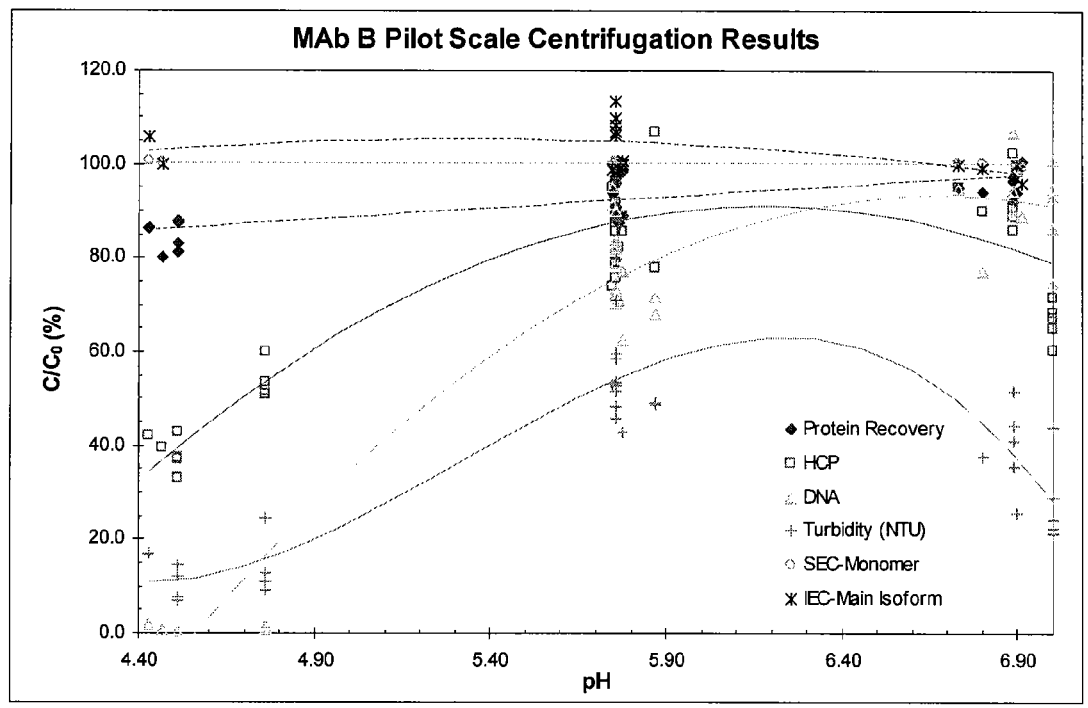

FIG. 9 represents the effects of various pH levels on the isolating monoclonal antibody B after centrifugation. The diamonds represent recovery of antibody B, the squares represents host cell protein concentrations, the triangles represent DNA concentrations, the plus signs (+) represent turbidity measurements, the circles (○) represent SEC monomers, and the Xs represent IEC main isoforms.

Figure 10:
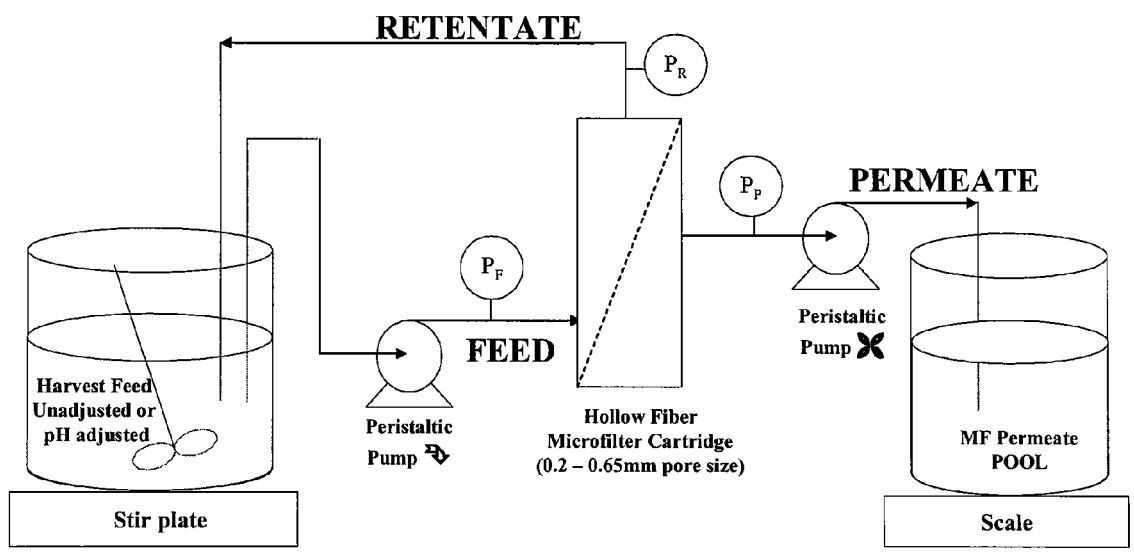

FIG. 10 shows a schematic of a microfiltration system. The objective of this system operation is to remove cells and other debris from the cell culture in advance of chromatographic purification. The clarification is performed using microfilters (0.2-0.65 μm nominal pore size) in a crossflow configuration (harvest feed and retentate stream flow parallel to the membrane surface). This system includes a peristaltic pump to circulate the feed through the microfiltration (MF) cartridges; however, other pumps can be used such as a rotary lobe or diaphragm pump. During filtration, the elapsed time, permeate stream weight, and the cartridge inlet, outlet, and permeate stream pressures are monitored. After the cell culture conditioned medium is concentrated 5-7-fold, a constant volume diafiltration with a buffered solution (pH similar to the harvest feed pH) is performed to recover most of the remaining product. The permeate stream is drawn from the system at a constant flow rate and collected in a vessel. The temperature of the operation can occur between 2-26° C. The feed vessel contains either unadjusted or pH adjusted harvest feed and is agitated to prevent cell settling.

Figure 11:
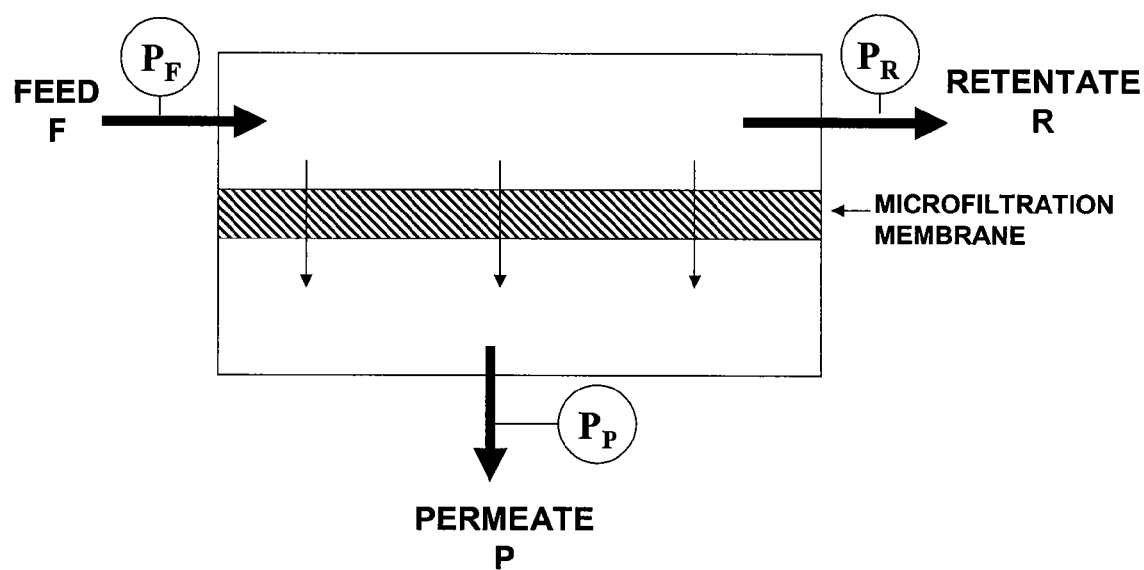

FIG. 11 shows the method for calculating the transmembrane pressure drop (TMP) across the microfilter. The TMP is calculated from the pressure measured on the harvest feed, retentate stream, and permeate stream sides. The pressure measurement is performed using a needle pressure gauge, a digital gauge, or a pressure transducer.

Figure 12:
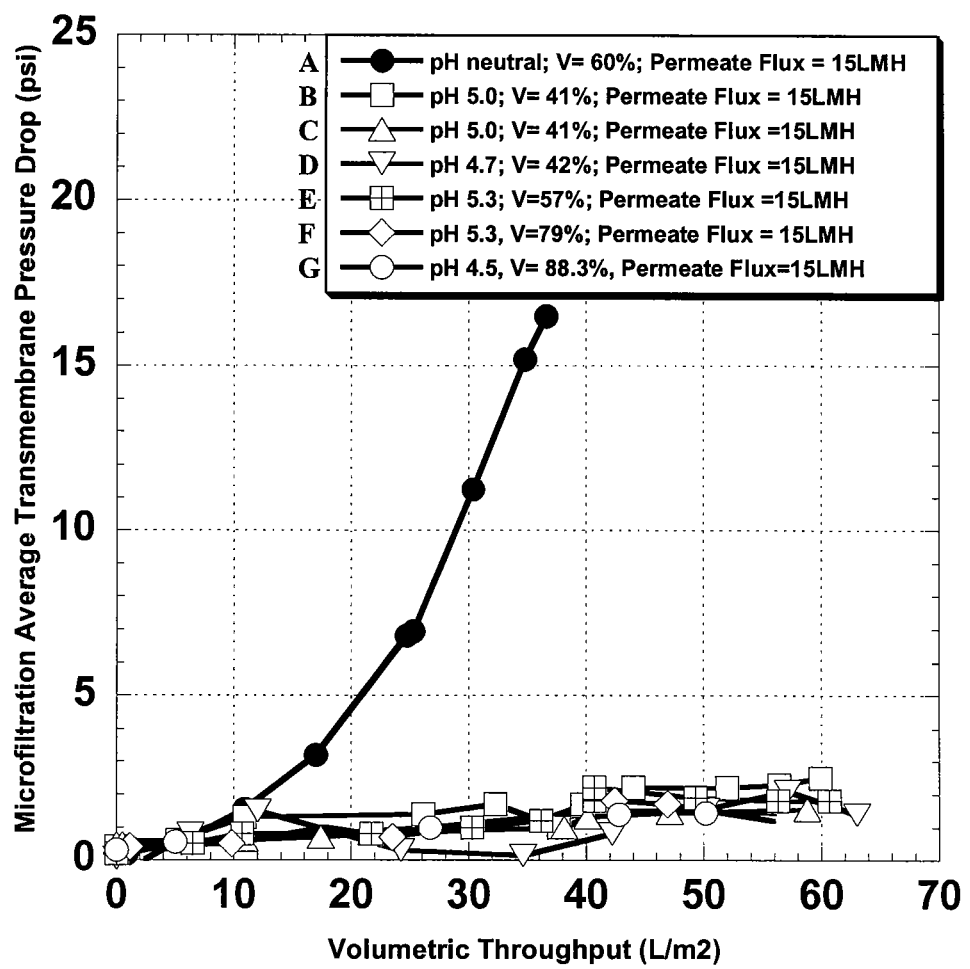

FIG. 12 represents the effect of pH adjustment on microfiltration operational performance. The y-axis represents the microfiltration filter average transmembrane pressure difference (TMP) in psi using 0.65 μm pore size hollow fiber filters; the x-axis represents the ratio of the volume of harvest feed loaded on the membrane to the area of the membrane ($L/m^2$). The harvest material used for these microfiltration experiments comprises Chinese Hamster Ovary cells that produce a glycosylated humanized monoclonal antibody (IgG1). The legend of FIG. 12 shows data for various pH adjusted harvest streams, and various percent cell viabilities. The graph shows that filtering unadjusted harvest feed which is lowered from neutral Bioreactor conditions to a pH of 4.7-5.3 results in a lower overall transmembrane pressure across the filters relative to filtering harvest feed which remains at a pH ranging between 6.8 and 7.2. The data indicates that lowering the pH of the harvest streams allows for reduced fouling of the filters at a set permeate flux (as indicated by the lower TMP at high loading), resulting in a more robust microfiltration operation.

Figure 13:
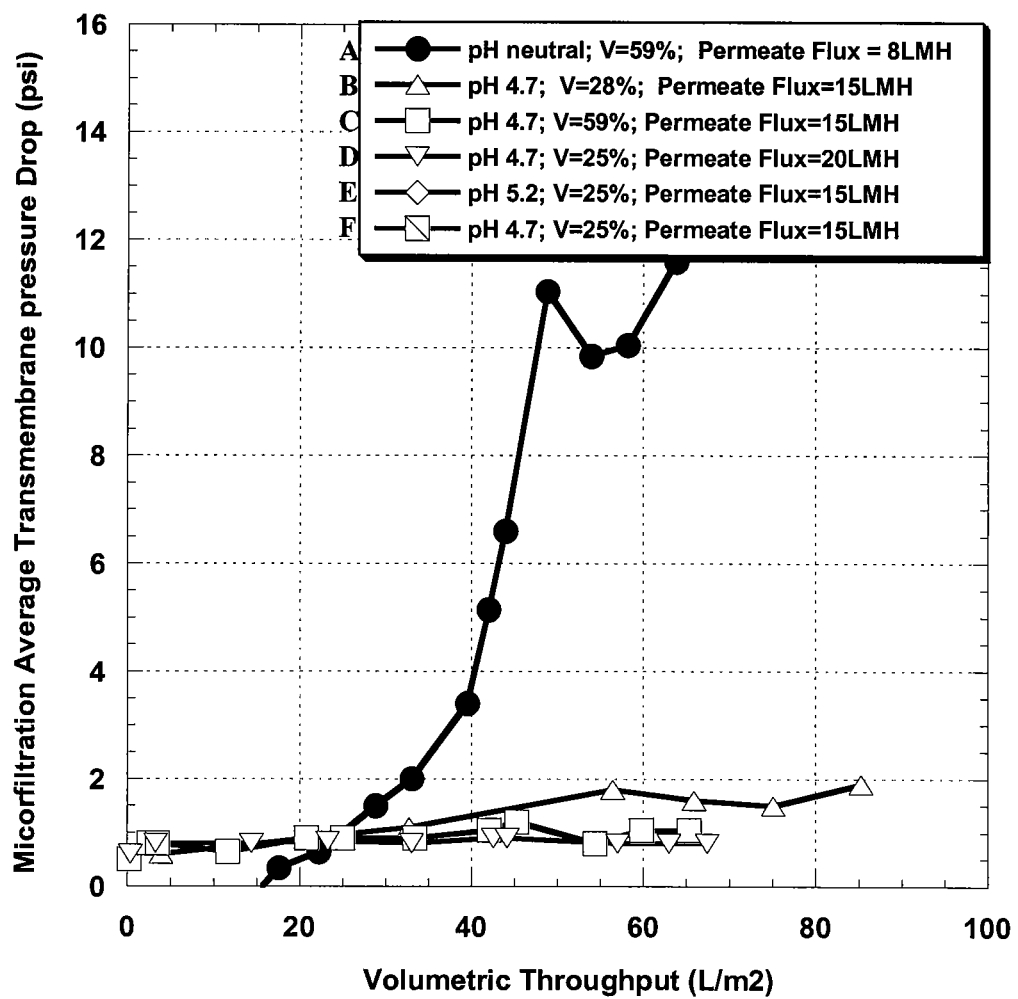

FIG. 13 represents the effect of pH adjustment on microfiltration operational performance similar to FIG. 12 but for another monocolonal antibody. The y-axis represents the microfiltration filter average transmembrane pressure difference (TMP) in psi using 0.65 μm pore size hollow fiber filters; the x-axis represents the ratio of the volume of harvest feed loaded on the membrane to the area of the membrane ($L/m^2$). The harvest material used for these microfiltration experiments comprises Chinese Hamster Ovary Cells that produce a well differentiated humanized, monoclonal antibody. The FIG. 13 legend shows data for various pH adjusted harvest streams, and various percent Cell Viabilities. The graph shows that filtering harvest feed which is lowered from neutral Bioreactor conditions to a pH of 4.7-5.2 results in a lower overall transmembrane pressure across the filters relative to filtering unadjusted harvest feed which remains at a pH ranging between 6.8 and 7.2. The data indicates that lowering the pH of the harvest streams allows for reduced fouling of the filters at a set Permeate flux (as indicated by the lower TMP at high loading). This results in a more robust microfiltration operation.

Figure 14:
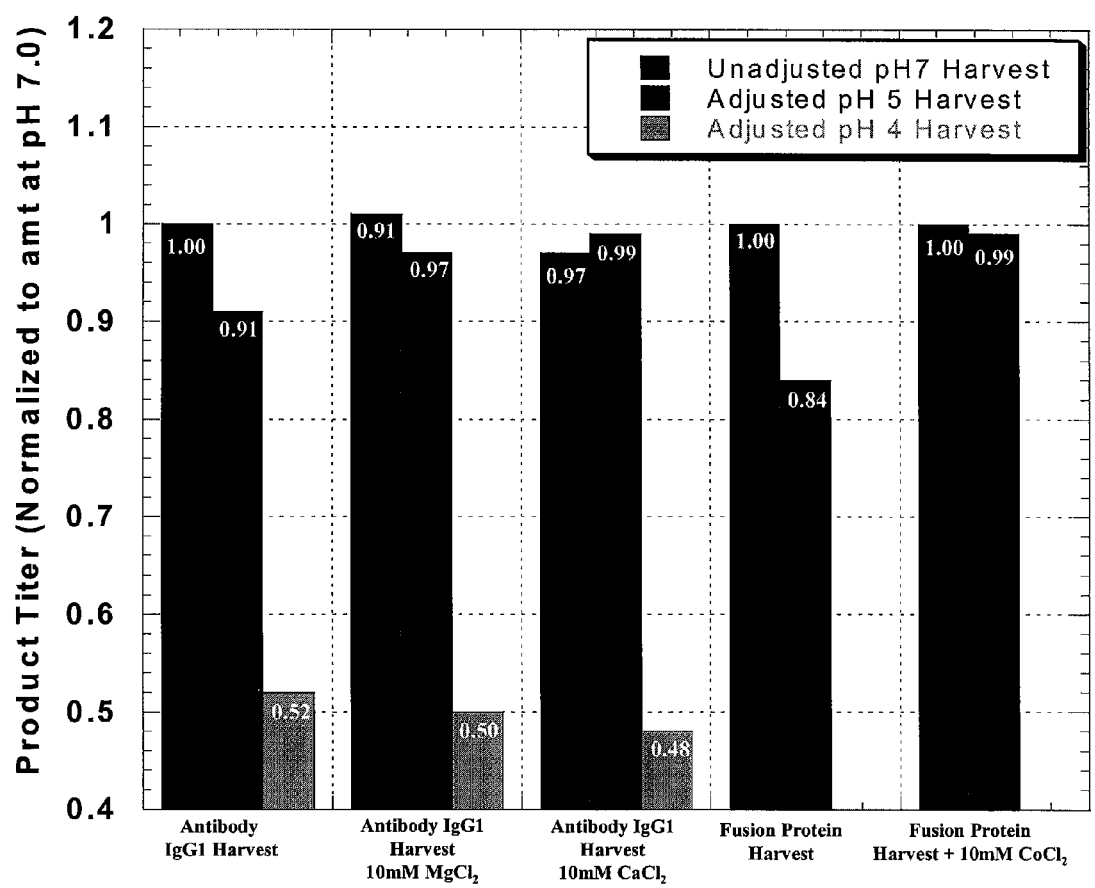

FIG. 14 represents the effects of pH change and the presence of different divalent cations on the product protein titer in the conditioned harvest stream The y-axis represents the product titer, normalized to the titer of pH 7.0 harvest which has no cations added. The x-axis represents the harvest streams for various biomacromolecules at several pH values (pH 7, 5, or 4) and types of divalent cations. The data for the fusion protein demonstrates that addition of $Co^{2+}$ during the pH 5 adjustment preserves the fusion protein in solution or eliminates possible protein co-precipitation with the flocculated cells and cell debris. The data for the antibodies demonstrates that addition of $Mg^{2+}$ or $Ca^{2+}$ during the pH 5 adjustment preserves the antibodies in solution or eliminates possible co-precipitation with the flocculated cells and cell debris.

Figure 15:
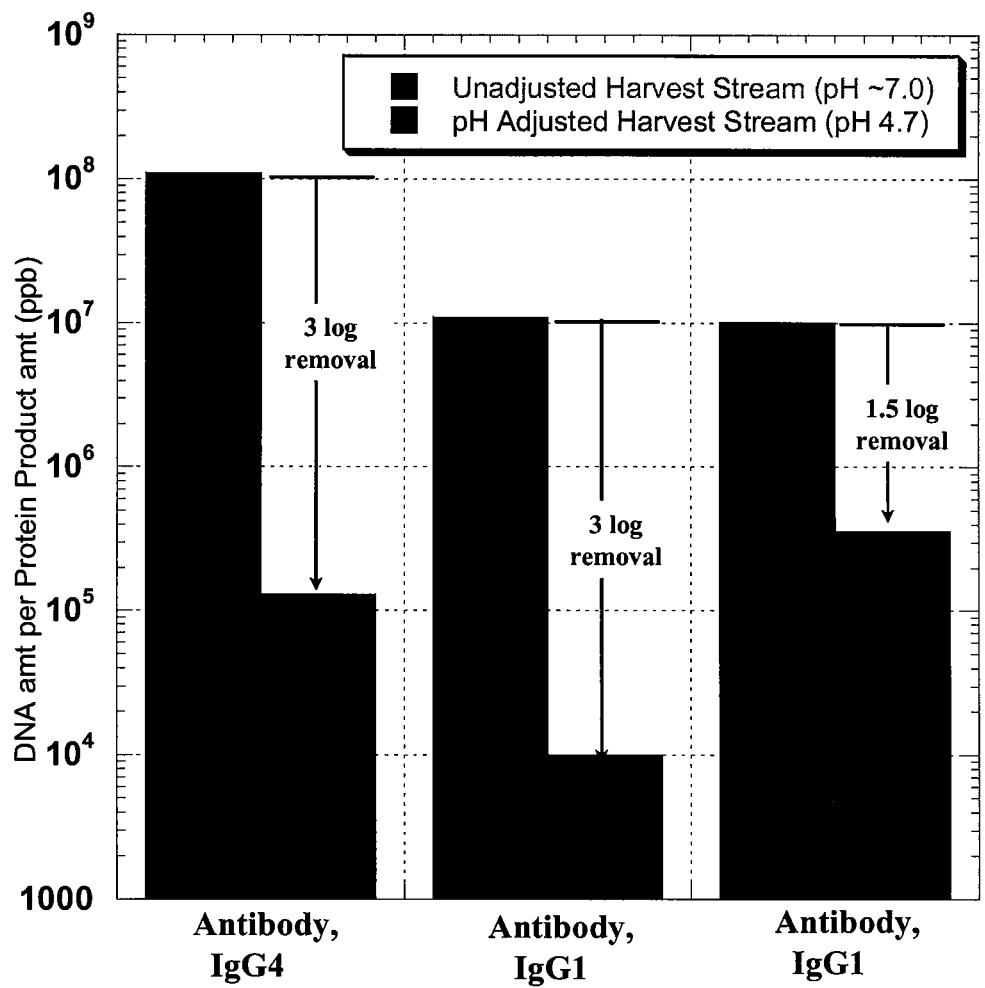

FIG. 15 represents the effect of harvest pH adjustment on DNA removal for different harvest streams containing various antibodies. The y-axis shows the amount of DNA impurity present (μg) per amount of antibody present (kg) in the clarified harvest stream. The x-axis represents the harvest/antibody stream both unadjusted and pH adjusted to pH 4.7 with 25% acetic acid. For all antibodies shown below, the adjustment of harvest pH from about 7.0 to 4.7 effectively brings about precipitation of DNA, resulting in a clarified harvest stream having 1.5 to 3 logs reduction in DNA impurity levels.

Figure 16:
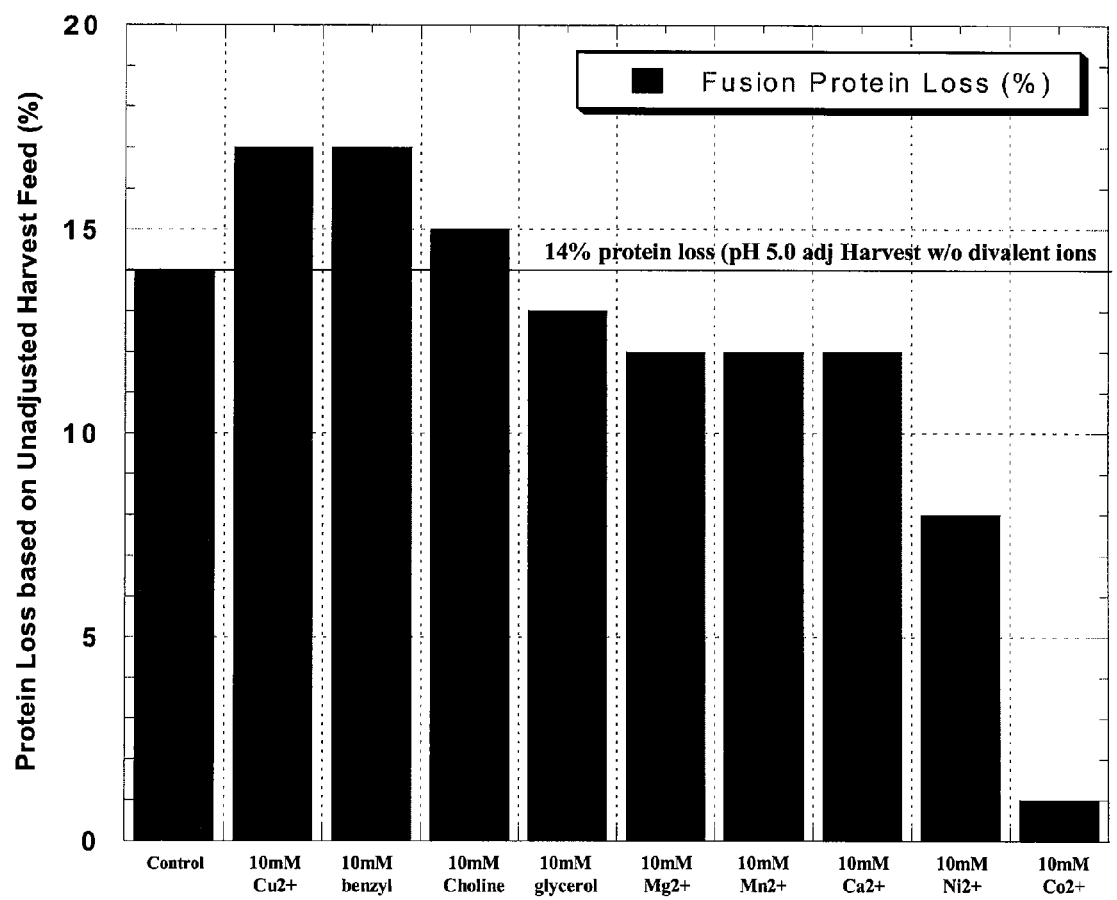

FIG. 16 represents the effect of adding various cations to the harvest feed followed by pH 5 adjustment of the harvest. The y-axis shows the loss in % protein based on the unadjusted harvest stream with or without the presence of additional ions. The first bar on the left of the graph represents protein loss of 14% (due to precipitation) after pH harvest adjustment to pH 5.0 without any additional divalent ions. The remaining bars represent additional protein loss (>14%) or protein product regain (<14%) in the presence of various divalent cations. The data shows that the presence of various transition metal ions such as $Ni^{2+}$, $Ca^{2+}$, $Mg^{2+}$, $Mn^{2+}$, and $Co^{2+}$ improve protein recovery.

Figure 17:
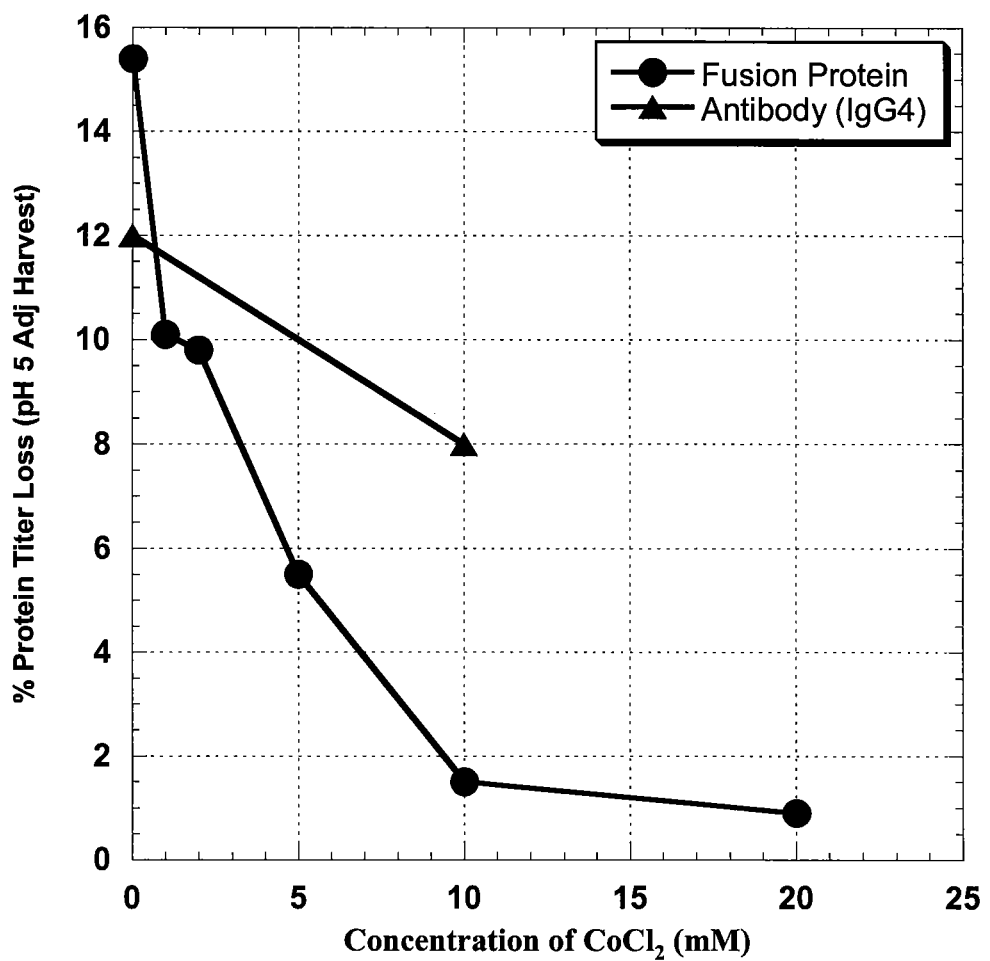

FIG. 17 represents the effect of $CoCl_2$ concentration on protein titer recovery from a harvest stream that is pH adjusted to 5.0 with 25% acetic acid. The y-axis represents the loss in % protein of the pH adjusted harvest stream at various levels of $CoCl_2$. The x-axis represents the concentration of $CoCl_2$ (mM) present in the pH 5.0 adjusted harvest stream. The data show that as the concentration of $Co^{2+}$ ions increases, the % loss of protein product due to pH induced precipitation decreases. An equilibrium concentration of 10 mM is shown for the fusion protein.

Figure 18:
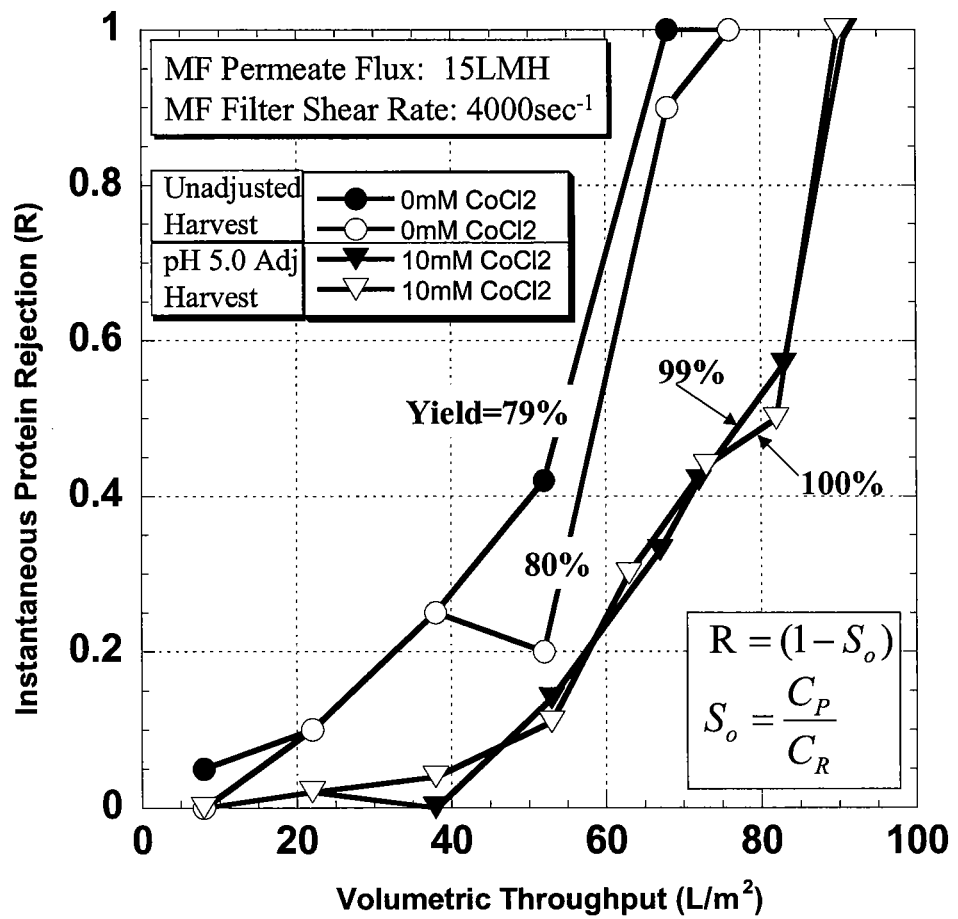

FIG. 18 represents the effect of the method of the present invention on filter protein rejection and overall clarification recovery. The y-axis represents the instantaneous filter protein rejection defined by the retention coefficient (R). The x-axis represents the volumetric throughput during the clarification operation of the composition comprising the biomacromolecule of interest. Data is shown for four separate MF experiments: the runs shown by the open and filled triangles represent harvest streams that have been pH 5.0 adjusted including the addition of 10 mM $CoCl_2$; and the runs shown by the open and filled circles represent unadjusted harvest streams with no $CoCl_2$ added. The data shows the MF retention coefficient is lower for pH adjusted harvest feed containing 10 mM $CoCl_2$ for all loading ratios studied. The data indicates that runs containing the $Co^{2+}$ divalent ions show complete recovery of the desired protein as compared to the 20% yield loss with the runs using unadjusted harvest feed.

DETAILED DESCRIPTION OF THE INVENTION

The present invention is directed to a method of isolating a biomacromolecule in a composition containing an impurity, the method comprising: (a) lowering the pH of the composition; (b) adding a divalent cation to the composition; and (c) separating the biomacromolecule from the impurity. The inventors of the present invention found that when attempting to separate (by filtration) an industrial-scale amount of antibody from a bioreactor containing cell culture with an initial high density of biological material, the transmembrane pressure drop across the filter increased significantly, presumably as a result of fouling of the membrane surface due to the high concentration of cellular material. Increased filter fouling in turn adversely impacted quantity of the antibody recovered, lowered clarification yields, and resulted in relatively higher impurity levels in the permeate stream. In some cases, the transmembrane pressure increased to values beyond the mechanical capabilities of the filter, thus causing the operation to stop before completion and resulting in significantly lower product yield.

In order to reduce filter transmembrane pressure, increase protein recovery in the permeate stream, and decrease the amount of impurities in the permeate stream, the method of the present invention lower the pH of the harvest feed before filtration, causing flocculation of large cells and cellular debris along with precipitation of other impurities (such as DNA). It was found that flocculation of impurities (cells, cellular debris and DNA) into large particles improved mass transfer of the composition near the surface of the filter, thus reducing transmembrane pressure across the filter at a predetermined permeate stream flux or flowrate. In addition, co-precipitation of impurities caused by dropping the harvest stream pH results in better retention of these impurities on the filter, and thus a reduction of impurity levels in the permeate stream.

Lowering the pH of the composition was found to induce precipitation of the desired antibody in the harvest feed, resulting in retention of the desired antibody by the membrane and reducing the amount of the desired antibody in the permeate stream. The method of the present invention further provides that the addition of divalent cations to pH-adjusted harvest feed prior to filtration selectively reduces the coprecipitation of the antibody and increases the amount of antibody recovered in the permeate stream, while not impacting the amount of impurities.

The methods of the present invention are useful for isolating biomacromolecules from impurities in a composition. Examples of biomacromolecules, e.g., antibodies, recombinant proteins, fusion proteins, etc., having similar solubility properties at low pH in the presence of divalent cations.

It is to be noted, unless otherwise clear from the context, that the term "a" or "an" entity refers to one or more of that entity; for example, "a protein," is understood to represent one or more proteins. As such, the terms "a" (or "an"), "one or more," and "at least one" can be used interchangeably herein.

The terms "isolating" and "isolation" refer to separating a biomacromolecule from at least one other undesired component or impurity found in the composition. The term "isolating" includes "purifying" and "clarifying." No particular level of isolation of a biomacromolecule is required, however in some embodiments, at least 50%, 70%, 80%, 90%, or 95% (w/w) of an impurity is separated from the biomacromolecule. For example, in some embodiments, isolation of a biomacromolecule would comprise separating the biomacromolecule from 80% of the HCP present originally in the composition.

The terms "clarifying" and "clarification" refer to the removal of large particles from a composition. For example, as applied to cellular cultures and growth media, the term "clarifying" refers to, e.g., the removal of prokaryotic and eukaryotic (e.g., mammalian) cells, lipids, and/or nucleic acids (e.g., chromosomal and plasmid DNA) from the cell culture. In some embodiments, the method of the present invention comprises (a) lowering the pH of the composition, allowing an impurity to flocculate within the composition, (b) adding a divalent cation to the composition; and (c) separating the biomacromolecule from an impurity in the composition. No particular level of flocculation of an impurity is required, however in some embodiments, at least 50%, 70%, 80%, 90%, or 95% (w/w) of an impurity is flocculated. For example, in some embodiments, clarification of a biomacromolecule would comprise flocculating 80% of the mammalian cells present in a composition. Flocculation can be measured by methods known to those in the art, including spectrophotographic methods such as a turbidimeter.

The terms "purifying" and "purification" refer to separating the biomacromolecule of the invention from an impurity or other contaminants in the composition, regardless of the size of the impurity. Thus, the term purification would encompass "clarification," but it would additionally encompass impurities smaller in size than those removed during clarification, e.g., proteins, lipids, nucleic acids, and other forms of cellular debris, viral debris, contaminating bacterial debris, media components, and the like. No particular level of purification of a biomacromolecule is required, however in some embodiments, at least 50%, 70%, 80%, 90%, or 95% (w/w) of an impurity is purified from the biomacromolecule. For example, in some embodiments, purification of a biomacromolecule would comprise separating the biomacromolecule from 80% of the HCP present originally in the composition.

The terms "biological biomacromolecule" or "biomacromolecule" as used herein refer to a molecule with a molecular mass exceeding 1 kDa which can be isolated from an organism or from cellular culture, e.g., eukaryotic (e.g., mammalian) cell culture or prokaryotic (e.g., bacterial) cell culture. In some embodiments, the use of the term refers to polymers, e.g., biopolymers such as nucleic acids (such as DNA, RNA), polypeptides (such as proteins), carbohydrates, and lipids. In some embodiments, the term "biomacromolecule" refers to a protein. In some embodiments, the term "biomacromolecule" refers to a recombinant protein or a fusion protein. In some embodiments, the protein is soluble. In some embodiments, the biomacromolecule is an antibody, e.g., a monoclonal antibody.

As used herein, the term "protein" is intended to encompass a singular "protein" as well as plural "proteins." Thus, as used herein, terms including, but not limited to "peptide," "polypeptide," "amino acid chain," or any other term used to refer to a chain or chains of amino acids, are included in the definition of a "protein," and the term "protein" may be used instead of, or interchangeably with, any of these terms. The term further includes proteins which have undergone post-translational modifications, for example, glycosylation, acetylation, phosphorylation, amidation, derivatization by known protecting/blocking groups, proteolytic cleavage, or modification by non-naturally occurring amino acids. Proteins also include polypeptides which form multimers, e.g., dimers, trimers, etc. The term protein also includes fusions proteins, e.g., a protein that is produced via a gene fusion process in which a protein (or fragment of a protein) is attached to an antibody (or fragment of antibody). Examples of fusion proteins of the present invention include disulfide-linked bifunctional proteins comprised of linked Fc regions from human IgG1 and human IgE; and lymphotoxin beta receptor immunoglobulin G1.

Antibodies can be purified according to the method of the present invention. The term "antibody" refers to polyclonal, monoclonal, multispecific, human, humanized or chimeric antibodies, single chain antibodies, Fab fragments, F(ab')2 fragments, fragments produced by a Fab expression library, anti-idiotypic (anti-Id) antibodies (including, e.g., anti-Id antibodies to antibodies of the invention), and epitope-binding fragments of any of the above. In some embodiments, the term "antibody" refers to a monoclonal antibody. The term "antibody" also refers to immunoglobulin molecules and immunologically active portions of immunoglobulin molecules, i.e., molecules that contain an antigen binding site that immunospecifically binds an antigen. The immunoglobulin molecules that can be purified by the method of the invention can be of any type (e.g., IgG, IgE, IgM, IgD, IgA and IgY), class (e.g., IgG1, IgG2, IgG3, and IgG4) or subclass of immunoglobulin molecule. Antibodies of the present invention also include chimeric, single chain, and humanized antibodies. Examples of antibodies of the present invention include commercialized antibodies, such as natalizmab (humanized anti-a4 integrin monoclonal antibody), humanized Anti-Alpha V Beta 6 monoclonal antibody, humanized anti-VLA1 IgG1 kappa monoclonal antibody; huB3F6 (humanized IgG1/kappa monoclonal antibody).

Antibodies purified by the method of the invention may be from any animal origin including birds and mammals. Preferably, the antibodies purified by the method of the invention are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins. See, e.g., U.S. Pat. No. 5,939,598 by Kucherlapati et al. In some embodiments, the antibody include, but are not limited to, IgG1, IgG2, IgG3, and IgG4 antibodies, including commercialized antobodies, such as natalizmab (TYSBARI®, Elan Pharmaceuticals, San Diego, Calif.).

Antibodies that can be purified by the method of the invention include, e.g., native antibodies, intact monoclonal antibodies, polyclonal antibodies, multispecific antibodies (e.g., bispecific antibodies) formed from at least two intact antibodies, antibody fragments (e.g., antibody fragments that bind to and/or recognize one or more antigens), humanized antibodies, human antibodies (Jakobovits et al., *Proc. Natl. Acad. Sci. USA* 90:2551 (1993); Jakobovits et al., *Nature* 362:255-258 (1993); Bruggermann et al., *Year in Immunol.* 7:33 (1993); U.S. Pat. Nos. 5,591,669 and 5,545,807), antibodies and antibody fragments isolated from antibody phage libraries (McCafferty et al., *Nature* 348:552-554 (1990); Clackson et al., *Nature* 352:624-628 (1991); Marks et al., *J. Mol. Biol.* 222: 581-597 (1991); Marks et al., *Bio/Technology* 10:779-783 (1992); Waterhouse et al., *Nucl. Acids Res.* 21:2265-2266 (1993)). The antibodies purified by the method of the invention may be recombinantly fused to a heterologous polypeptide at the N- or C-terminus or chemically conjugated (including covalently and non-covalently conjugations) to polypeptides or other compositions. For example, antibodies purified by the method of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

In some embodiments, the biomacromolecule or composition of the present invention is pharmaceutically acceptable. "Pharmaceutically acceptable" refers to a biomacromolecule or composition that is, within the scope of sound medical judgment, suitable for contact with the tissues of human beings and animals without excessive toxicity or other complications commensurate with a reasonable benefit/risk ratio.

In some embodiments, the biomacromolecule is a soluble protein. The term "soluble" refers to the propensity of a protein to substantially localize to the hydrophilic or aqueous-based environments of a cellular host, e.g., the cytoplasm, periplasm or extracellular medium. Thus, during cellular fractionation, a soluble protein would generally be substantially isolated with the cytoplasmic, periplasmic, or extracellular components of a host cell. In some embodiments, a soluble protein is water soluble in the absence of detergents. One of skill in the art will recognize that neither the cellular localization of a polypeptide, nor the cellular fractionation of a protein, is absolute. Thus, the phrase "substantially localize" refers to a protein in which 50%, 70%, 75%, 80%, 85%, 90%, 95%, or 99% of the protein is in the designated cellular location, e.g., cytoplasm, periplasm, or extracellular medium.

The term "composition" in the present invention refers to a mixture of one or more molecules of the biomacromolecule of the present invention and optionally at least one impurity, wherein the impurity and the biomacromolecule are not the same. In some embodiments, the composition comprises a biomacromolecule, a cellular host organism (e.g., mammalian cells), and a growth media sufficient for propagating the host organism and allowing expression of the biomacromolecule of interest. The selection and use of growth medium are known to those in the art. In some embodiments, the growth media is a cell culture media. Cell culture media vary according to the type of cell culture being propagated. In some embodiments, the cell culture media is a commercially available media. In some embodiments, the composition comprises a growth media which contains e.g., inorganic salts, carbohydrates (e.g., sugars such as glucose, galactose, maltose or fructose) amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum. newborn calf serum and horse serum), trace elements (e.g., zinc, copper, selenium and tricarboxylic acid intermediates) and combinations thereof. Examples of growth medias include, but are not limited to, basal media (e.g., MEM, DMEM, GMEM), complex media (RPMI 1640, Iscoves DMEM, Leibovitz L-15, Leibovitz L-15, TC 100), serum free media (e.g., CHO, Ham F10 and derivatives, Ham F12, DMEM/F12). Common buffers found in growth media include PBS, Hanks BSS, Earles salts, DPBS, HBSS, EBSS. Media for culturing mammalian cells are well known in the art and are available from, e.g., Sigma-Aldrich Corporation (St. Louis, Mo.), HyClone (Logan, Utah), Invitrogen Corporation (Carlsbad, Calif.), Cambrex Corporation (E. Rutherford, N.J.), JRH Biosciences (Lenexa, Kans.), Irvine Scientific (Santa Ana, Calif.), and others. Other components found in growth media can include ascorbate, citrate, cysteine/cystine, glutamine, folic acid, glutathione, linoleic acid, linolenic acid, lipoic acid, oleic acid, palmitic acid, pyridoxal/pyridoxine, riboflavin, selenium, thiamine, transferrin. One of skill in the art will recognize that there are modifications to growth media which would fall within the scope of this invention.

In some embodiments, the composition further comprises a harvest feed. The term "harvest feed" refers to a media in which cells are present in immediately before harvesting, or a media in which harvested cells are placed immediately after harvesting and into which the cells are resuspended. A harvest feed can include any of the compositions listed above for growth media, or other media suitable for resuspending the harvested cells or cellular fractions. For example, in some embodiments, the harvest media may contain water, a buffer, osmotic agents, anti-degradation agents, etc.

The term "impurity" refers to one or more components of the composition that is different from the biomacromolecule of the present invention. In some embodiments, the impurity can include an intact mammalian cell (e.g., Chinese hamster ovary cells (CHO cells) or murine myeloma cells (NSO cells)), or partial cells, e.g., cellular debris. In some embodiments, the impurity comprises a protein (e.g., soluble or insoluble proteins, or fragments of proteins, such as HCP), lipid (e.g., cell wall material), nucleic acid (e.g., chromosomal or extrachromosomal DNA), ribonucleic acid (t-RNA or mRNA), or combinations thereof, or any other cellular debris that is different from the biomacromolecule of interest. In some embodiments, the impurity can originate from the host organism that produced or contained the biomacromolecule of interest. For example, an impurity could be a cellular component of a prokaryotic or eukaryotic cell (e.g., cell wall, cellular proteins, DNA or RNA, etc.) that expressed a protein of interest. In some embodiments, the impurity is not from the host organism, e.g., an impurity could be from the cell culture media or growth media, a buffer, or a media additive. The impurity as used herein can include a single undesired component, or a combination of several undesired components.

The biomacromolecule of the present invention can be isolated from a cell culture comprising growth media and various eukaryotic cells, e.g., mammalian cells. The mammalian cells of the present invention, including the mammalian cells that are used in the methods of the invention, are any mammalian cells that are capable of growing in culture. Exemplary mammalian cells include, e.g., CHO cells (including CHO-K1, CHO DUKX-B11, CHO DG44), VERO, BHK, HeLa, CV1 (including Cos; Cos-7), MDCK, 293, 3T3, C127, myeloma cell lines (especially murine), PC12, HEK-293 cells (including HEK-293T and HEK-293E), PER C6, Sp2/0, NSO and W138 cells. Mammalian cells derived from any of the foregoing cells may also be used.

The biomacromolecule of the present invention can be isolated from a cell culture comprising growth media and various prokaryotic cells, e.g., *E. coli, Bacillus subtilis, Salmonella typhimurium* and various species within the genera *Pseudomonas*, e.g., *P. aeruginosa*, yeast cells, e.g., *Saccharomyces, Pichia, Hansenula, Kluyveromyces, Schizosaccharomyces, Schwanniomyces* and *Yarrowia*, insect cells, e.g., *Trichoplusia, Lipidotera, Spodoptera, Drosophila* and Sf9, or plant cells, e.g., *Arabidopsis*. One of skill in the art can select an appropriate cell line depending on the biomacromolecule of interest.

In the present invention, the pH of the composition is adjusted to a pH lower than that of the harvest feed. Compositions of the present invention, e.g., those comprising a harvest feed, generally have a pH of about 6.0 to about 8.0, about 6.5 to about 7.5 or about 6.8 to about 7.2 without adjustment. In some embodiments, any pH lower than the pH of the harvest feed is used in the isolation of the present invention. In some embodiments, the pH of the composition is lowered to a pH within a range of about 1.0 to about 6.0, about 2.0 to about 5.5, about 3.0 to about 6.5, about 3.0 to about 5.0, about 4.0 to about 5.0, about 4.0 to about 4.7, about 4.3 to about 5.0, or about 4.7 to about 5.0. In some embodiments, the pH of the composition is lowered to within a range of about 4.0 to about 4.7. In some embodiments, the pH can be lowered to a pH of about 3.5. For some biomacromolecules, a pH lower than 3.5 results in denaturation or instability of the biomacromolecule of interest, and thus is not desireable. While not being bound by any theory, in some embodiments the lowering of harvest feed pH flocculates one or more components of the composition, predominantly cells and cellular debris. In some embodiments, host cell DNA is flocculated, enabling easier and/or more efficient isolation of the biomacromolecule of interest. In some embodiments, host cell proteins are flocculated, enabling enabling easier and/or more efficient isolation of the biomacromolecule of interest. In some embodiments wherein filtration is used to isolate the biomacromolecule, the aggregated large particles reduce the fouling of the pores of a filter, thus allowing for greater filtering efficiency, lower transmembrane pressures, and higher throughput volumes. In some embodiments, the present invention is directed to a method of isolating a biomacromolecule by lowering the pH.

The pH of the composition of the present invention can be adjusted by various means. In some embodiment, the pH is lowered by addition of an acid to the composition. Suitable acids include, but are not limited to, strong acids such as perchloric acid ($HClO_4$), hydroiodic acid (HI), hydrobromic acid (HBr), hydrochloric acid (HCl), nitric acid ($HNO_3$), sulfuric acid (diprotic) ($H_2SO_4$), or weak acids such as acetic acid ($CH_3COOH$) (e.g., glacial acetic acid), citric acid ($C_6H_8O_7$), formic acid (HCOOH), hydrocyanic acid (HCN), hydrogen sulfate ion ($HSO_4^-$), or combinations of any of the acids listed above. In some embodiments, the pH of the composition can be adjusted by use of buffers, such as phosphate buffers (e.g., sodium and potassium phosphates), bicarbonate buffers, citrate buffers, borate buffers, acetate buffers, tromethamine buffers, HEPES buffers, and combinations thereof.

While not being bound by any theory, in some embodiments of the present invention, the lowering of the pH aids in aggregating large impurity particles, thereby reducing "fouling," i.e., plugging or filling the pores, of the filter. Increased filter fouling can adversely impact recovery of a desired biomacromolecule in the permeate stream, resulting in low clarification yields and relatively higher impurity levels in the permeate stream. In some cases, the fouling of the filter increases transmembrane pressure. Fouling of the filter may increase transmembrane pressure value beyond the mechanical capabilities of the filter, thus causing the filter operation to be stopped before completion and resulting in significantly lower product recovery. Thus, in some embodiments the present invention is directed to a method of isolating a greater amount or volume of biomacromolecule in a composition, by lowering the pH of the composition. In some embodiments, the lowered pH can increase the purity and quality of the biomacromolecule recovered.

In some embodiments, the lowering of the pH of the composition results in coprecipitation of the biomacromolecule of interest as well as the impurity, resulting in reduced recovery of the biomacromolecule in the extracellular media. Inventors of the present invention have found that in some embodiments, addition of divalent cations to the pH-adjusted composition is suitable for increasing the recovery of the biomacromolecule of interest. The term "increased recovery" refers to a comparison of method of the present invention relative to an identical method of purifying but without the addition of divalent cations. For example, if Method A is the method of the present invention (except it does not comprise addition of divalent cations to the harvest feed) and yields 100 mg of the biomacromolecule of interest, and Method B is identical to Method A (except Method B comprises addition of divalent cations to the harvest feed) and yielded 110 mg of biomacromolecule, then it would be determined that Method B has an "increased recovery" of 10%. In some embodiments, the method of the present invention increases recovery of the biomacromolecule by greater than 3%, 4%, 5%, 6%, 7%, 8%, 9%, 10%, 15%, 20% or 25%. In some embodiments, the method of the present invention increases recovery up to 10%, 15%, 20%, 25%, 30% or 50%.

In the present invention, a divalent cation is added to the composition. Various divalent cations exist and are known to those in the art, and include, e.g., calcium cation ($Ca^{2+}$), magnesium cation ($Mg^{2+}$), copper cation ($Cu^{2+}$), cobalt cation ($Co^{2+}$), manganese cation ($Mn^{2+}$), nickel cation ($Ni^{2+}$), berylium cation ($Be^{2+}$), strontium cation ($Sr^{2+}$), barium cation ($Ba^{2+}$), radium cation ($Ra^{2+}$), zinc cation ($Zn^{2+}$), cadmium cation ($Cd^{2+}$), silver cation ($Ag^{2+}$), palladium cation ($Pd^{2+}$), rhodium cation ($Rh^{2+}$), and combinations thereof. One of skill in the art will realize that the cation can exist in salt form, e.g., a calcium salt such as $CaCl_2$ can produce a calcium cation when placed in an aqueous solution. Thus, as used herein, the phrase "adding a divalent cation" would encompass not only the addition of a cation in its charged stated, but also the addition of a salt or other compound that would produce a divalent cation upon introduction into the composition of the present invention. In some embodiments, the divalent cation is $Co^{2+}$ or $Ni^{2+}$, or their salts (e.g., $CoCl_2$, $NiCl_2$, $CaCl_2$, $MnCl_2$, $MgCl_2$, and $CuCl_2$), or combinations of one or more of these cations or salts. It is to be expected that certain divalent cations may be more suitable for different biomacromolecules. However, one of skill in the art can easily and quickly test many divalent cations to determine which achieves the maximum recovery of the biomacromolecule of interest.

Various concentrations of divalent cations in the composition are suitable for use in the present invention. On of skill in the art will recognize that various amounts of divalent cations are normally present in small amounts in the harvest feed (endogenous divalent cations), and that various amounts of divalent cations can be added to the harvest feed in accordance with the present invention (exogenous divalent cations). In some embodiments, the concentration of the divalent cations comprises both exogenous and endogenous cations. However, for practical purposes, since the amount of endogenous is relatively small compared to the amount of exogenous divalent cations, the concentration of the divalent cations can be calculated by simply considering the exogenous divalent cations. In some embodiments, the divalent cation in the composition is present at a concentration of about 0.01 mM to about 1 M in the composition. In some embodiments, the divalent cation is present at a concentration of about 0.1 mM to about 500 mM, or about 0.5 mM to about 200 mM, about 1.0 mM to about 100 mM, about 2 mM to about 50 mM, about 5 mM to about 15 mM, or about 2 mM to about 20 mM in the composition. In some embodiments, the divalent cation is present at a concentration of about 10 mM in the composition. While not being bound by any methodology, a suitable concentration of divalent cation can be determined by method similar to that found in Example 14, wherein various concentrations of divalent cation are added to a pH-adjusted composition comprising a biomacromolecule, and then determining the lowest concentration at which a maximum amount of biomacromolecule can be recovered. One of skill in the art will understand that different concentrations of cations may be required for various biomacromolecules.

Various means can be used to separate the biomacromolecule of the present invention from one or more impurities. Examples of means of separating the biomacromolecule from an impurity include, without limitation, precipitation, immunoprecipitation, chromatography, filtration, centrifugation, and combinations thereof. In some embodiments, the separating of the biomacromolecule from the impurity is achieved by the use of a filter. The term "filtration" or "filtering" refers to the process of removing suspended particles from a composition by passing the composition through one or more semi-permeable membranes (or medium) of a specified pore size diameter. The term "permeate stream" when referring to filtration, refers to the fraction of the composition that passes through the filter pores during filtration. The term "retentate stream" when referring to filtration, refers to the fraction of the composition that remains on the filter or that does not pass through the filter pores during filtration. In some embodiments, after filtration the biomacromolecule of the present invention is substantially in the permeate stream (i.e., it passes through the filter pores and is collected), while an impurity (e.g., cellular debris, DNA, and/or HCP) is substantially in the retentate stream. In some embodiments, after filtration the biomacromolecule of the present invention is substantially in the retentate stream, while an impurity is substantially in the permeate stream. In some embodiments, "bench scale" filtration can be used to predict appropriate conditions for industrial scale filtration.

Suitable filter types, chemistries, and module configurations for purifying particular biomacromolecules are known to those in the art and can be selected based on various factors, e.g., the amount and size of the components of the composition to be filtered, the volume of the composition to be filtered, and the cell density and viability of the composition to be filtered. In some embodiments, filters, such as membrane filters, plate filters, cartridge filters, bag filters, pressure leaf filters, rotary drum filters or vacuum filters can be used. In some embodiments, a depth filter or a cross filter is used. The types of crossflow filter modules that apply in the present invention include hollow fiber, tubular, flat plate (plate-and-frame), spiral wound, or vortex flow (e.g., rotating) filter geometries. In some embodiments, a tangential flow filter is used. In some embodiments, hollow fibers, tubular, and flat-sheet membrane modules were utilized in a tangential-flow (cross-flow) mode. Commercially available filters that can be employed are manufactured for various manufacturing vendors such as Millipore Corporation (Billerica, Mass.), Pall Corporation (East Hills, N.Y.), GE Healthcare Sciences (Piscataway, N.J.), and Sartorius Corporation (Goettingen, Germany).

The pore diameter in the filters of the present invention can vary according to the type of biomacromolecule being isolated and the type of impurities present in the composition. In some embodiments, the filter pore diameters can be 0.1 μm to 1.0 μm, 0.2 μm to 0.8 μm, or 0.2 μm to 0.65 μm in diameter.

Movement of a composition, such as a harvest feed, through a filter during filtration generates a transmembrane pressure resulting from the membrane resistance. As the membrane surface becomes accumulated (or polarized) with cellular material, there is an increased resistance to flow across the membrane at a constant flowrate, thus causing the driving force or transmembrane pressure to increase. If the amount of cellular material near the surface of the membrane is reduced, or if the membrane is less polarized, the transmembrane pressure tends to remain substantially constant. Methods to calculate transmembrane potential are know to those in the art, and include the use of pressure transducers or gauges. In some embodiments of the present invention, the transmembrane pressure can be calculated by taking the difference between the average of the feed and retentate stream outlet pressure and the permeate stream pressure. FIG. 8 show a schematic of the transmembrane pressure calculation.

Generally, during filtration of a composition, e.g., a harvest feed, that has not been pH-adjusted, the transmembrane pressure of a filter increases significantly as more of the composition is loaded onto the filter. For example, in some embodiments the transmembrane pressure increases 5 psi, 7 psi, 10 psi, 15 psi or 20 psi or greater from the start of the filtration process (when the first amount of the composition is placed in the filter) to the end of the filtration process (typically following a 7-10× concentration of cellular material and a 3-5× diafiltration) as the pores of the filter become clogged. For example, as can be seen in FIG. 12 (Feed composition A) and FIG. 13 (Feed composition A), the transmembrane pressure during filtration of a harvest feed solution in which the pH has not been adjusted can increase from about less than 1 psi at the beginning of loading the harvest feed onto the filter to about greater than 10 psi after loading 60 liters/m2 of harvest feed onto a filter (a 1000% increase in transmembrane pressure). Thus, the term "substantially constant" where referring to the transmembrane pressure, refers to transmembrane pressures that do not increase greater than 4 psi, 3 psi, or 2 psi over the course of filtration. A substantially constant transmembrane pressure is exemplified by the harvest feed compositions B through G in FIG. 12 and feed compositions B through F in FIG. 13. Each of these compositions start at a transmembrane pressure of about less than 1 psi and over the course of filtration, the transmembrane pressure on the filters which are filtering these compositions do no exceed 2 psi. Thus, the transmembrane pressures on the filters which are filtering compositions B through G in FIG. 12 and feed compositions B through F in FIG. 13 are considered to be substantially constant. In some embodiments, the present invention is directed to a method of purifying a biomacromolecule in a composition, the method comprising (a) lowering the pH of the composition; (b) adding a divalent cation to the composition; and then (c) filtering the composition through a membrane, the filtering resulting in a transmembrane pressure, wherein the transmembrane pressure remains substantially constant during the filtering.

In some embodiments, the method of the present invention decreases protein filter rejection. The term "protein filter rejection" can be exemplified by the equation $R=(1-[C_P/C_R])$, wherein R represents protein filter rejection coefficient, $C_P$ is the instantaneous permeate concentration of the biomacromolecule of interest, and $C_R$ is the instantaneous retentate concentration of the biomacromolecule of interest. In some embodiments, the present invention is directed to a method of isolating a biomacromolecule in a composition comprising lowering the pH of the composition, adding a divalent cation to the composition, and filtering the biomacromolecule, wherein the value of the protein filter rejection coefficient is lower for a given volumetric throughput relative to a biomacromolecule in a composition without pH adjustment and/or divalent cation addition. See for example FIG. 18.

When isolating biomacromolecules, in some embodiments large volumes of a composition (e.g., harvest feed) can be present, e.g., during commercial manufacturing processes. Large volumes present several challenges for purification processes. For example, the effect that a small change in flow rate through a filter has on the recovery of an isolated biomacromolecule is amplified when large volumes are used. Likewise, when using large volumes, the effect that an increase in cell density in a harvest feed has on product recovery is also amplified. Thus, the use of large volumes of a composition present unique problems that are amplified and have greater ramifications relative to the use of smaller volumes. Thus, in some embodiments the present invention is directed to a method of isolating a biomacromolecule present in a large volume of a composition. The term "large volume" refers to volumes associated with the commercial and/or industrial production of a biomacromolecule. In some embodiments, the term "large volume" refers to 10 to 2000 liters, 20 to 1000 liters or 50 to 500 liters.

In some embodiments, it is beneficial or desirable to harvest a biomacromolecule from a high cell density composition (e.g., harvest feed). High cell density compositions present unique problems relative to normal cell density compositions. For example, high cell density compositions can have higher amounts of impurities present in the composition, thereby increasing the amount of impurities that need to be removed during the purification process. Thus, a higher cell density composition can foul a filter more quickly, thereby prohibiting filtration of the composition. In some embodiments, high cell density compositions require the use of more filters, or filters with larger surface areas. Both of these requirements can result in greater costs associated with filtration and/or loss of product. In the present invention, the pH of the composition is lowered, thereby removing some impurities, and allowing the purification of higher cell density compositions. Thus, some embodiments in the present invention are directed to a method of isolating a biomacromolecule present in a high cell density composition. The term "high cell density" generally refers to cell densities in a harvest feed of about $1 \times 10^5$ to $3.5 \times 10^7$, about $1.0 \times 10^6$ to about $1.0 \times 10^7$, or about $5.0 \times 10^6$ to about $9.0 \times 10^6$ cells per ml for mammalian cells. Of course, one of skill in the art will appreciate that various cells traditionally grow at different cell densities. Thus, in some embodiments, "high cell density" cell cultures refers to cell cultures containing cells at a density higher than the density traditionally practiced for that cell line.

In some embodiments of the present invention, the method of the present invention is directed to a method of increasing robustness of a filtration process, the method comprising (a) lowering the pH of a composition; (b) adding a divalent cation to the composition; and (c) filtering the composition through a membrane. The term "increase robustness" refers the ability to use a wider range of flow rates for a given filter while not increasing transmembrane pressure, impurity concentrations, or product loss. The term "increase robustness" also refers to the ability to filter a larger volume, or higher cell density, of harvest feed for a given filter while not increasing transmembrane pressure, impurity concentrations, or product loss.

In some embodiments of the present invention, the method is drawn to a method of clarifying a composition comprising a biomacromolecule, e.g., a harvest feed, prior to filtration, the method comprising (a) lowering the pH of the composition; (b) adding a divalent cation to the composition; and (c) separating the biomacromolecule from an impurity in the composition. In some embodiments, clarifying a composition correlates with a decrease in turbidty, as measured by a turbidimeter, such as a Hach 2100AN Turbidimeter (Hach Co., Loveland, Colo.).

In some embodiments, the method of the present invention comprises separating the biomacromolecule from an impurity by subjecting the composition to a centrifugal force (i.e., centrifugation), where centrifugation forms a supernatant and a precipitate. In some embodiments, the centrifugation forms a supernatant substantially free of an impurity (cells or cellular debris) and a concentrated cell/cellular debris precipitant. The term "precipitate," when referring to centrifugation, refers to the fraction of the composition that is precipitated (or pelleted) during centrifugation to form a cell/cell debris mass. The term "supernatant," refers to the fraction of the composition that is not precipitated (or pelleted) during centrifugation, for example, the fraction of the composition that remains in an aqueous phase in the composition and is substantially cell free. In some embodiments, after centrifugation the biomacromolecule of the present invention is substantially in the supernatant (i.e., it remains substantially suspended in the liquid fraction of the composition). In some embodiments, after centrifugation the biomacromolecule of the present invention is substantially in the precipitate (e.g., it is precipitated out of solution or is present in a pellet resulting from the centrifugation). In some embodiments, a density gradient is used to separate the biomacromolecule from the impurity. Thus, in some embodiments both the biomacromolecule and the impurity remain in the supernatant after centrifugation, albeit at different densities and thus different locations in the centrifugation apparatus.

Various centrifugation apparatuses can be used. In some embodiments, the centrifugation can be accomplished by disc stack centrifugation. In some embodiments, "bench scale" filtration can be used to predict appropriate conditions for industrial scale filtration. Centrifugation variables can be varied to achieve optimal isolation of the biomacromolecule of interest. For example, in some embodiments, various rotational speeds or flow rates can be used to increase the quality of biomacromolecule recovery, and/or the quantity of biomacromolecule recovery.

The steps of the method of the present invention can be ordered in various sequences. For example, in some embodiments of the present invention, the lowering the pH and the adding a divalent cation occurs before the separating the biomacromolecule away from the impurity. In some embodiments, the pH of the harvest media is adjusted first, the divalent cation is added, and then the biomacromolecule is separated from an impurity. In other embodiments, the divalent cation is added first, the pH of the composition is adjusted, and then the biomacromolecule is separated. In some embodiments, one or more purification procedures may occur between either (a) the lowering of the pH, (b) the adding of divalent cations, or (c) the separating the biomacromolecule away from the impurity. Alternatively, the steps (a), (b), or (c) of the method of the present invention can be contiguous, e.g., no additional purification procedures occur between steps (a), (b) and (c). However, when steps (a), (b) and (c) are contiguous, additional purification procedures can occur before or after steps (a), (b) and (c).

Some embodiments of the present invention are directed to a method for improving the operational robustness of the clarification during isolation of a biomacromolecule in a composition comprising the biomacromolecule and an impurity, the method comprising (a) lowering the pH of the composition; (b) allowing the impurity to flocculate, (c) adding a divalent cation to the composition; and (d) separating the biomacromolecule from an impurity in the composition. The term "operational robustness" refers to the ability of the isolation operation (e.g., the filtration process) to handle a wider variety of cell loads for a given separation apparatus (e.g., filter size). In some embodiments, the lowering of the pH reverses fouling of the filter membranes by impurities (e.g., cellular debris, etc.), thus allowing the filtration to operate under higher volume loading with higher throughput volumes.

EXAMPLES

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

Example 1

Figure 1:
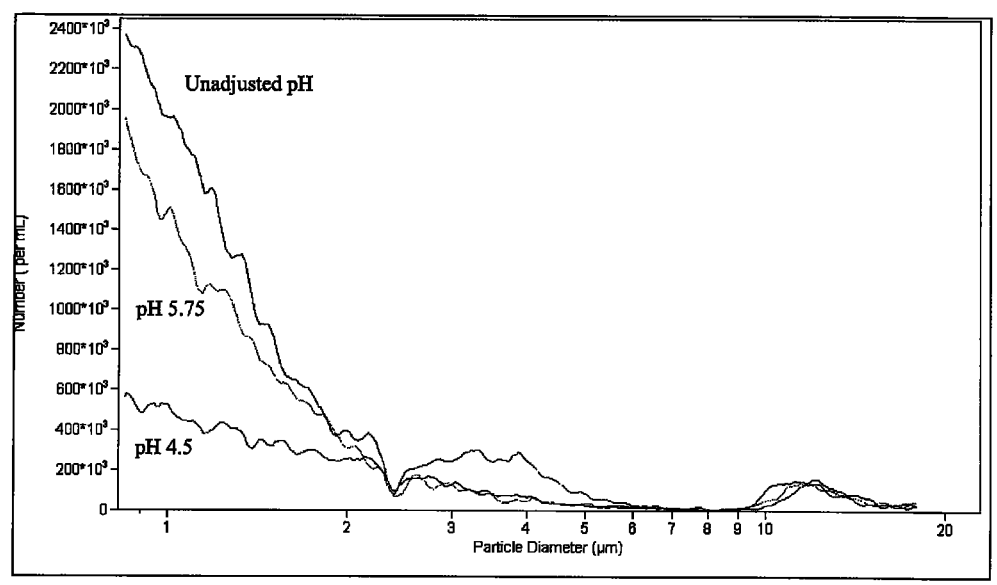
FIG. 1 shows analysis of particle size distribution for a monoclonal antibody (Mab) cell culture at a pH of 4.5, 5.75 and 7.1 (unadjusted). At pH 4.5, there is a pronounced decrease in the proportion of particles with less than a 2.5 μm diameter, and an increased population of particles from 2.5 to 6.0 μm.

The effects of pH on the flocculation of cells was investigated by comparing the particle size distributions of cultured cells at various pH levels. Cell culture fluid was harvested from two bioreactors, and then separated into three different groups, one control group and two experimental groups. The experimental groups were adjusted to approximately pH 4.5 or 5.75 using 25% acetic acid. The control group was left unadjusted at approximately pH 7.1. The samples of each group were then analyzed using the Beckman Coulter, Multisizer III (Fullerton, Calif.) and the average diameter was determined. Results are presented in FIG. 1.

The experimental results indicate that at a pH less than 5.75, there is a pronounced reduction of particles with a diameter less than 2.5 μm, and an increasing population of particles 2.5 to 6.0 μm.

Example 2

Figure 2:
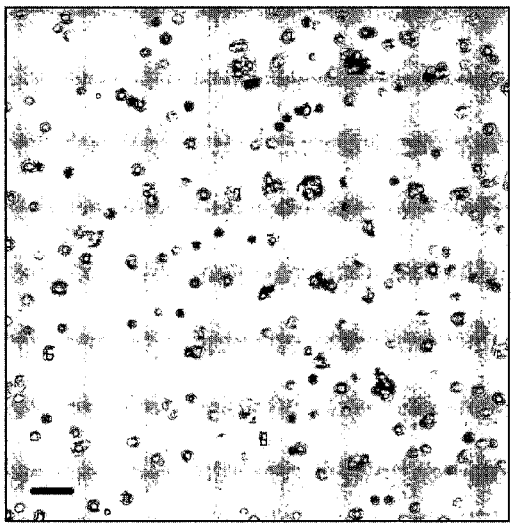
FIG. 2 represents magnified images of cells at a pH of 4.5 (FIG. 2c), 5.75 (FIG. 2b) and 7.1 (FIG. 2a), stained with Trypan Blue. The experimental images indicated increased staining at lower pH levels.
Figure 2:
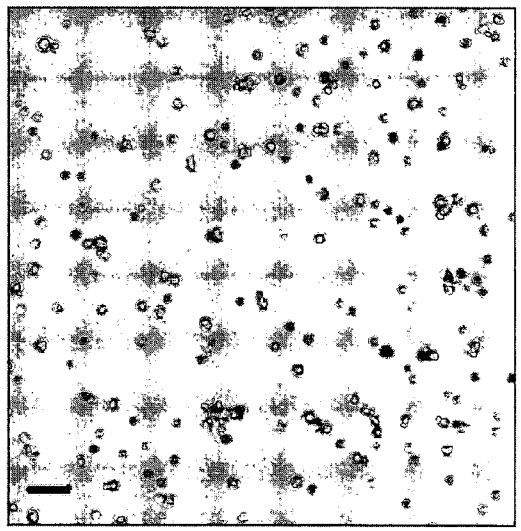
Figure 2:
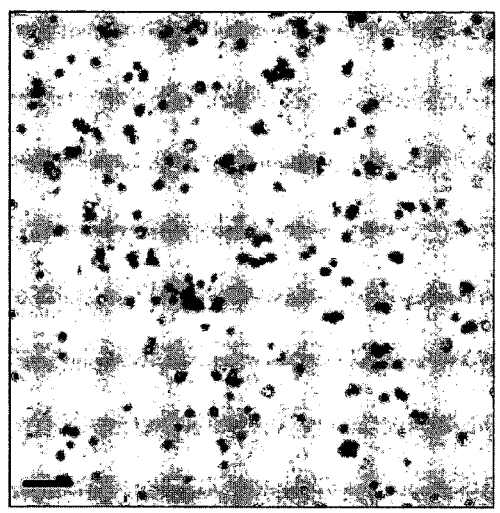

The effects of pH changes on the flocculation of cells was investigated by staining cells at various pH levels with Trypan Blue and analyzing them with a CEDEX cell analyzer (Flonamics, Madison Wis.). As described in Example 1, cell culture fluid was harvested from two bioreactors, and then separated into three different groups, one control group and two experimental groups. The experimental groups were pH adjusted to approximately 4.5 and 5.75 using 25% acetic acid. The control group was left unadjusted at approximately pH 7.1. TB stain was then added, and analyzed using magnified images. Results are presented in FIG. 2.

TB dye stained dead cells by permeating through and staining intracellular proteins. The data presented for cells at pH 4.50 shows many more stained particulates per unit area relative to that of pH 7.00 and 5.75. This suggests that not only TB stained dead cells, but also other protein aggregates of similar sizes are being stained. This observation further supports the hypothesis that precipitation and flocculation of proteins takes place at the lower pH.

Example 3

Figure 3:
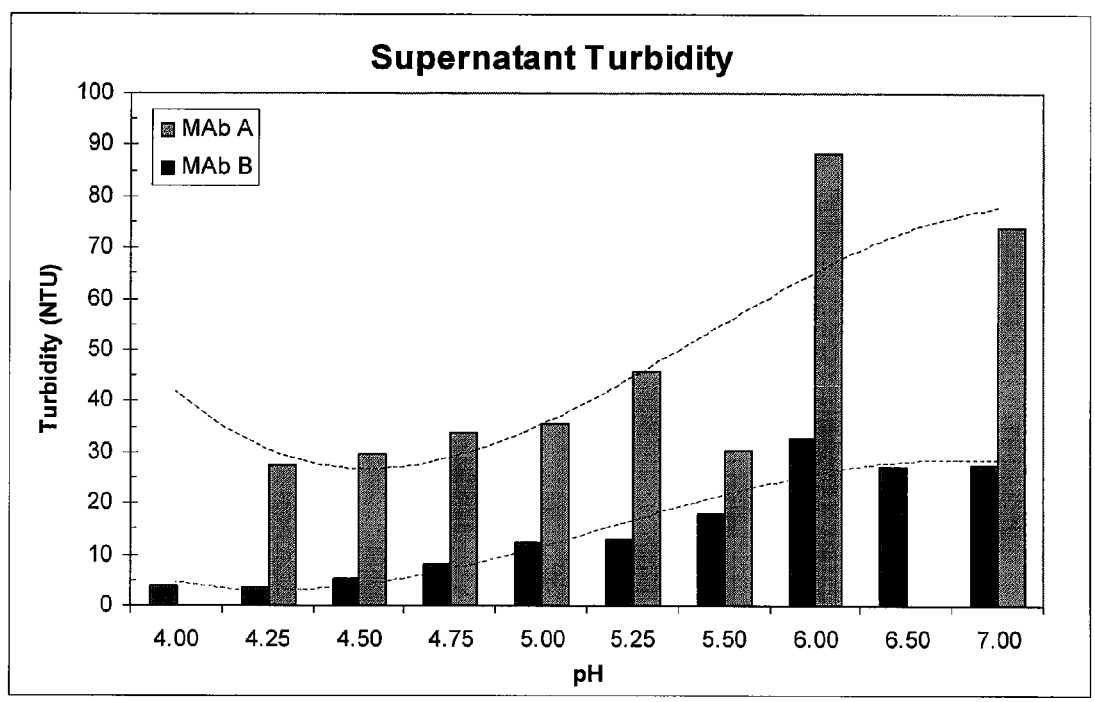
FIG. 3 shows supernatant turbidity in cell culture as a function of a decrease in pH. Generally, the turbidity is reduced at lower pH levels due to cellular and particle flocculation.

The effects of pH changes on supernatant turbidity was determined. Cell cultures were divided into various aliquots, and then adjusted to a pH of 4.25, 4.5, 4.75, 5.0, 5.25, 5.5, 6.0 or unadjusted (pH 7.1). Settling velocity experiments were then performed, and the turbidity of the resulting supernatant was measured. The results are presented in FIG. 3.

The experimental results indicate the supernate turbidity increase with increase in pH level. This suggests that at lower pH ranges, the cells are flocculating and being removed during the settling velocity experiments.

Example 4

IgG1 and IgG4 class monoclonal antibodies were produced by recombinant Chinese Hamster Ovary (CHO) or murine (NSO) cell fermentation. A vial of Master Cell Bank cells was thawed and expanded via various shaker flasks and bioreactor sizes in the inoculum preparation. The inoculum preparation and production bioreactor medium was made using animal-free components. Temperature, pH and dissolved oxygen levels were controlled in all bioreactor stated.

Example 5

The harvest feed of Example 4 was either (a) not pH-adjusted, or (b) adjusted to a pH of 4.7. The adjusted (or unadjusted) harvest feed was then passed through a microfilter in a tangential-flow filtration mode at a constant recirculation and permeate flowrate. The transmembrane pressure during the filtration process was calculated (see FIG. 11) for both the pH-adjusted harvest feed and the non-pH adjusted harvest feed. Results of the measurement of transmembrane pressure are provided for IgG1 class antibody and IgG4 class antibody in FIG. 12 and FIG. 13, respectively. The figures demonstrate that the lowering of a harvest feed to a pH ranging from 4.7 to 5.3 results in a low and relatively constant transmembrane pressure when the harvest feed is applied to a filter, whereas a harvest feed that is not pH adjusted does result in a sharp increase in transmembrane pressure when applied to a filter.

While not being bound by a particular theory, the evidence suggests that the lowering of the pH resulted in increased flocculation of cellular material, resulting in larger particles which were less likely to interfere with the pores on the microfilter. The clarification was performed in crossflow mode where the harvest feed was directed into the microfiltration module containing microporus membranes, the retained cells and cellular debris were retained and recirculated back into the feed vessel while the cell-free permeate passed across the filter membrane and was collected (see FIG. 10 for schematic). The permeate was drawn from the system at a constant flow rate and collected in a vessel. The separation by microfiltration of a desired protein from a bioreactor containing cell culture with an initial high density of biological material, resulted in an increased transmembrane pressure drop across the microfilter as a result of fouling of membrane filter surface by high concentration of cellular material. In order to reduce the filter transmembrane pressure drop to increase robustness of the microfiltration operation and increase protein recovery in the permeate, the pH of the harvest feed was lowered to 4.0-5.0 before microfiltration. The lowering of the pH caused flocculation of large cells and cellular debris along with precipitation of impurities (such as DNA). The flocculation of impurities (cells, cell debris and DNA) into large particles improved mass transfer of the composition near the surface of the filter thus reducing the pressure drop driving forces across the filter at a predetermined permeate flux or flowrate (See FIGS. 3 and 4).

Example 6

The effect of lowering pH levels on removal of host cell proteins and DNA was investigated. FIG. 5 demonstrations that lower pH levels increase both host cell protein and DNA removal from a solution. Cell cultures were divided into different aliquots, then the pH of the sample of each aliquot was adjusted. The samples were then centrifuged, and the amount of host cell protein or DNA was determined. The data indicates that host cell proteins were reduced by greater than 50% at a pH of less than 5.0, while DNA was reduced by greater than 90% at a pH of less than 5.0. It is likely that these impurities precipitate out of solution and are removed by the centrifugation.

Example 7

The effect of lowering pH on the quality and recovery of two monoclonal antibodies was investigated. FIG. 6 indicates that protein recovery of both monoclonal antibodies decreased below pH 6.0 by 5% to 10%, and decreased greatly for antibody A below 4.5. This dramatic decrease in protein recovery was accompanied by increased levels of aggregate and acidic variants, illustrated here by decreasing monomer and main isomform levels, indicating molecular instability at low pH. Antibody B showed no significant degradation over the pH range observed.

Example 8

The effect of lowering pH on the efficiency of a hollow fiber microfiltration (MF) was investigated. FIG. 7 demonstrates that microfiltration harvest product quality and impurity results agreed will the results of FIG. 5, with host cell proteins and DNA being reduced by 50% and 90% respectively at pH less than 5.0. Clarified turbidity levels were lower than initial experiments of FIG. 3 due to the filtration process involved with the microfiltration unit operation. Still, the results indicate greater than a 2-fold reduction in turbidity with cell culture conditioning to lower pH levels.

Bench scale MF yield results are illustrated in FIG. 8. Results illustrate yield losses below pH 4.5 as seen during initial conditioning experiments. Additionally, substantial losses were observed at pH 5.5 or higher due to membrane fouling during MF processing. Flocculation effects provided by cell culture conditioning at lower pH levels reduce this plugging.

Example 9

The effect of lowering pH on harvesting a monoclonal antibody was investigated. Antibody B centrifugation results also agreed with the clarification results of FIG. 3 and FIG. 5. Overall yield numbers for bench scale centrifuge runs were lower than initial clarification experiments due to the additive product losses from conditioning and the centrifugation unit operation. Also, turbidity levels were higher than clarification experiments due to shear difference between bench and pilot scale centrifuges. However, both of these process outputs follow the same trends seen during clarification experiments. Increased variability in the centrifuge data points was due to varied centrifuge operating conditions.

Example 10

The effect of lowering pH levels on the turbidity of the harvest feed of Example 4 was determined. The pH of the harvest feed containing either $MgCl_2$, $CaCl_2$, or NaCl was either (1) not adjusted (pH 6.9-7.2), (2) adjusted to a pH of 6.0, (3) adjusted to a pH of 5.0, (4) adjusted to a pH of 5.0, (5) adjusted to a pH of 4.5, or (6) adjusted to a pH of 4.0. The data was generated by pH adjusting aliquots of harvest feed to the specified pH using 25% v/v acetic acid, allowing the flocculation and settling of the cellular mass to occur for about 2 to 24 hrs and measuring the turbidity (degree of clarity) of the clear supernatant using a turbidimeter. A general reduction in supernatant turbidity occurred as the pH of the adjusted harvest material dropped, indicating a clearer supernatant at lower pH values (see FIG. 4). This reduction in turbidity was a result of a higher degree of cellular flocculation that occured at lower pH levels, resulting in more rapid settling of cellular mass. The flocculation and improved settling provided for more efficient microfiltration operational performance (see FIG. 12 or FIG. 13).

Example 11

The effect of pH adjustment on the recovery of DNA contaminants from the harvest feed was determined by collecting the harvest feed as described in Example 4 and then either (a) not adjusting the pH of the harvest feed, or (b) lowering the pH of the harvest feed to 4.7. Both the adjusted and the unadjusted harvest feed was then allowed to settle for 24 hours. Samples were taken of the clear supernatant and tested for DNA. The amount of DNA remaining in the cell free harvest was determined by Quantitative Polymerase Chain Reaction (QPCR). FIG. 15 demonstrates that there is about a 1.5 to 3 log reduction in DNA contaminants in the harvest feed that has been adjusted to a pH of 4.7 relative to a harvest feed that has not been pH adjusted.

Example 12

The effect of pH adjustment on the recovery of a monoclonal antibody (IgG4) and a fusion protein was determined by collecting the harvest feed as described in Example 4. The harvest feed was then adjusted to a pH of either 7.0, 5.0 or 4.0 and allowed to settle for 2-24 hours. Samples were taken of the clear supernatant and tested for protein titer. The amount of antibody or fusion protein present in the cell-free harvest feed was then determined by Protein G titer assay. FIG. 14 shows the effects of pH change on the product protein titer in the conditioned Harvest stream. Data is shown for an IgG4 class antibody and a fusion protein. The data for both types of proteins demonstrate that there was significant reduction in protein as the pH drops from 7.0 to 4.0. The amount of protein loss due to pH induced precipitation ranged from 3% to 52%. The method of determining protein concentration of the composition was based on affinity capture of the antibody or fusion protein on Protein G coupled HPLC resin.

Example 13

The effect of addition of divalent cations to pH-adjusted harvest feed on protein was investigated by adding 10 mM of various divalent cations to the harvest feed, and then lowering the pH of the harvest feed to 5.0. The resulting harvest feed was allowed to settle for 2-24 hours. Samples were taken of the clear supernatant and tested for protein titer. The titer was compared to a control experiment (pH 5.0 adjusted harvest with no divalent cations). The amount of antibody or fusion protein present in the cell-free harvest feed was determined by Protein G titer assay. FIG. 16 demonstrates that addition of divalent cations generally reduced the loss of soluble antibody compared to the control run without any additional ions. The y-axis represent a normalized titer, which is represented by (titer in filtered harvest feed that has been treated with cation) divided by (titer in filtered harvest feed that has not been treated with cation).

Example 14

The effect of various concentrations of divalent cations added to pH-adjusted harvest feed was investigated. Specifically, $CoCl_2$ (or $Co^{2+}$) was added to a final concentration of 1 mM, 2 mM, 5 mM, 10 mM or 20 mM in pH-adjusted harvest feed. The amount of product recovered from the pH-adjusted harvest feed was then assayed using Protein G to determine the effect of the various concentrations of $CoCl_2$ on product recovery. FIG. 17 demonstrates that about 10 mM of $CoCl_2$ was sufficient to minimize product loss (or maximize product yield recovery) after pH adjustment.

Example 15

The effects of the method of the present invention on protein filter rejection was investigated as a function of cumulative volume processed through a microporous membrane throughout the concentration and diafiltration phases. The protein filter rejection coefficient was determined by measuring the retentate and permeate titers at various time intervals and calculating the protein filter rejection coefficient with the equation $R=(1-[C_P/C_R])$. Data is shown for four separate MF experiments: the runs shown by the open and filled triangles represent harvest streams that have been pH 5.0 adjusted including the addition of 10 mM CoCl2; and runs shown by the open and filled circles represent unadjusted harvest streams with no presence of CoCl2. The data shows the MF retention coefficient is lower for pH adjusted harvest feed containing 10 mM CoCl2 for all loading ratios studied. For example, at typical large-scale loading ratios of 60-70 L/m2, the calculated rejection coefficients are ~30% compared to nearly complete rejection (90-100%) for the runs that were not pH adjusted. Also shown in FIG. 6 are overall protein recoveries from each microfiltration run. The runs containing the $Co^{2+}$ divalent ions show complete recovery of the desired protein as compared to the 20% yield loss with the runs using unadjusted harvest feed The effects of the method of the present invention on protein filter rejection was investigated as a function of cumulative volume processed through a microporous membrane throughout the concentration and diafiltration phases. The protein filter rejection coefficient was determined by measuring the retentate and permeate titers at various time intervals and calculating the protein filter rejection coefficient with the equation $R=(1-[C_P/C_R])$. The data presented in FIG. 18 is from four separate microfiltration experiments: in C and D, 10 mM $CoCl_2$ was added to the harvest stream during pH adjustment; in A and B, no $CoCl_2$ was added. All harvest feeds were lowered to a pH of 5.0. FIG. 18 demonstrates that the microfiltration retention coefficient was lower for harvest feeds adjusted with 10 mM $CoCl_2$ for all loading ratios studied. For example, at typical large-scale loading ratios of 60-70 $L/m^2$, the calculated rejection coefficients for microfiltration runs C and D were ~30% compared to nearly complete rejection (90-100%) for the runs A and B. FIG. 18 also demonstrates the overall protein recovery from each microfiltration run. The runs containing the $Co^{2+}$ divalent ions (C and D) showed close to complete recovery of the desired protein, whereas runs in which no $Co^{2+}$ was added (A and B) resulted in a 20% yield loss.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method of purifying a composition containing a recombinant protein and an impurity, the method comprising:
 (a) lowering the pH of the composition to a pH range of about 3.0 to about 6.5;
 (b) adding a divalent cation selected from the group consisting of $Co^{2+}$, $Ni^{2+}$ and combinations thereof to the composition to result in a divalent cation concentration of about 1 mM to about 50 mM; and
 (c) separating the protein from the impurity,
 wherein the protein comprises an antibody or a fusion protein comprising an Fc region, which is produced by a recombinant eukaryotic host cell,
 wherein the composition comprises a harvest feed of the recombinant eukaryotic host cell,
 wherein the addition of the divalent cation increases the recovery of the protein by greater than 3% compared to the amount of protein recovered without the addition of the divalent cation, and
 wherein the separating of (c) is performed by subjecting the composition to centrifugation, the centrifugation forming a supernatant and a precipitate wherein the protein is substantially in the supernatant, or wherein the separating of (c) is performed by filtering the composition, the filtering forming a permeate stream and a retentate stream wherein the protein is substantially in the permeate stream, and wherein (a) and (b) are carried out sequentially in any order before (c).

2. The method of claim 1, wherein the divalent cation is $Co^{2+}$.

3. The method of claim 2, wherein the addition of the divalent cation increases the recovery of the protein by greater than 10%.

4. The method of claim 1, wherein the pH of the composition in (a) is lowered to a pH range of about 3.0 to about 5.0.

5. A method of clarifying a recombinant protein in a composition containing an impurity, the method comprising:
(a) lowering the pH of the composition to a pH of about 5.0;
(b) adding a divalent cation selected from the group consisting of $Co^{2+}$, $Ni^{2+}$, and combinations thereof to the composition to result in a divalent cation concentration of about 1 mM to about 100 mM; and
(c) separating the protein from the impurity,
wherein the protein comprises an antibody or a fusion protein comprising an Fc region, which is produced by a recombinant eukaryotic host cell,
wherein the composition comprises a harvest feed of the recombinant eukaryotic host cell,
wherein the addition of the divalent cation increases the recovery of the protein by greater than 3% compared to the amount of protein recovered without the addition of the divalent cation,
wherein the separating of (c) is performed by subjecting the composition to centrifugation, the centrifugation forming a supernatant and a precipitate wherein the protein is substantially in the supernatant, or wherein the separating of (c) is performed by filtering the composition, the filtering forming a permeate stream and a retentate stream wherein the protein is substantially in the permeate stream, and wherein (a) and (b) are carried out sequentially in any order before (c), and
wherein the composition comprising the harvest feed is clarified.

6. The method of claim 5, wherein the adding the divalent cation to the composition results in a divalent cation concentration of about 2 mM to about 50 mM.

7. The method of claim 5, wherein the separating in (c) is performed by filtering the composition, wherein the filtering results in a transmembrane pressure; and wherein the transmembrane pressure remains substantially constant during the filtering.

8. A method of isolating a recombinant protein in a composition containing an impurity, the method comprising:
(a) lowering the pH of the composition to a pH range of about 3.0 to about 6.5;
(b) adding a divalent cation selected from the group consisting of $Co^{2+}$, $Ni^{2+}$, and combinations thereof to the composition to result in a divalent cation concentration of about 1 mM to about 100 mM; and
(c) separating the protein from the impurity,
wherein the protein comprises an antibody or a fusion protein comprising an Fc region, which is produced by a recombinant eukaryotic host cell,
wherein the addition of the divalent cation increases the recovery of the protein by greater than 3% compared to the amount of protein recovered without the addition of the divalent cation, and
wherein the separating of (c) is performed by subjecting the composition to centrifugation, the centrifugation forming a supernatant and a precipitate wherein the protein is substantially in the supernatant, or wherein the separating of (c) is performed by filtering the composition, the filtering forming a permeate stream and a retentate stream wherein the protein is substantially in the permeate stream, and wherein (a) and (b) are carried out sequentially in any order before (c).

9. The method of claim 8, wherein the pH of the composition in (a) is lowered at least 1 pH unit.

10. The method of claim 8, wherein the pH of the composition in (a) is lowered to a pH range of about 3.0 to about 5.0.

11. The method of claim 10, wherein the pH of the composition in (a) is lowered to a pH of about 5.0.

12. The method of claim 8, wherein the adding the divalent cation to the composition results in a divalent cation concentration of about 2 mM to about 50 mM.

13. The method of claim 8, wherein the separating in (c) is performed by filtering the composition, wherein the filtering results in a transmembrane pressure; and wherein the transmembrane pressure remains substantially constant during the filtering.

14. The method of claim 8, wherein
(a) the pH of the composition is lowered to a pH of 4.7 to 5.5;
(b) the adding the divalent cation to the composition results in a divalent cation concentration of about 2 mM to about 50 mM; and
(c) the separating is performed by filtering the composition.

15. The method of claim 14, wherein the divalent cation is $Co^{2+}$.

16. The method of claim 14, wherein the filtering is performed by a tangential-flow filter.

17. The method of claim 8, wherein the impurity is selected from the group consisting of a protein, lipid, nucleic acid, ribonucleic acid, and combinations thereof.

18. The method of claim 8, wherein the addition of the divalent cation increases the recovery of the protein by greater than 10%.

19. The method of claim 1, wherein the separating in (c) is performed by filtering the composition.

20. The method of claim 1 wherein adding the divalent cation comprises adding a salt comprising the divalent cation.

21. The method of claim 5 wherein adding the divalent cation comprises adding a salt comprising the divalent cation.

22. The method of claim 8 wherein adding the divalent cation comprises adding a salt comprising the divalent cation.

23. The method of claim 14, wherein adding the divalent cation comprises adding a salt comprising the divalent cation.

24. The method of claim 23, wherein the salt is selected from the group consisting of $CoCl_2$, $NiCl_2$, and combinations thereof.

* * * * *